US012620151B2

(12) United States Patent
Jiang et al.

(10) Patent No.: US 12,620,151 B2
(45) Date of Patent: May 5, 2026

(54) SYSTEMS AND METHODS FOR MAGNETIC RESONANCE IMAGING

(71) Applicant: SHANGHAI UNITED IMAGING HEALTHCARE CO., LTD., Shanghai (CN)

(72) Inventors: Boyu Jiang, Shanghai (CN); Jianmin Yuan, Shanghai (CN); Wending Tang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 935 days.

(21) Appl. No.: 17/658,827

(22) Filed: Apr. 12, 2022

(65) Prior Publication Data

US 2022/0383561 A1     Dec. 1, 2022

(30) Foreign Application Priority Data

May 18, 2021     (CN) .......................... 202110539454.6

(51) Int. Cl.
  *G06T 11/00*        (2006.01)
  *A61B 5/00*        (2006.01)
        (Continued)

(52) U.S. Cl.
  CPC ............ *G06T 11/003* (2013.01); *A61B 5/055* (2013.01); *G01R 33/48* (2013.01);
        (Continued)

(58) Field of Classification Search
  CPC ................ G06T 11/003; G06T 7/0012; G06T 2207/10081; G06T 2211/424;
        (Continued)

(56) References Cited

U.S. PATENT DOCUMENTS 8,334,694 B2 *  12/2012  Tan ...................... G01R 33/243
                                                324/309
2005/0264287 A1 *  12/2005  Griswold ........... G01R 33/5611
                                                324/309
        (Continued)

FOREIGN PATENT DOCUMENTS

CN          105548927  A        5/2016
CN          107907846  A        4/2018
        (Continued)

*Primary Examiner* — Emily C Terrell
*Assistant Examiner* — Daniella M. DiGuglielmo
(74) *Attorney, Agent, or Firm* — METIS IP LLC

(57) ABSTRACT

The present disclosure provides a system and method for magnetic resonance imaging. The method may include obtaining a first set of imaging data, the first set of imaging data being sampled in multiple shots, each shot of the multiple shots corresponding to a plurality of echo times, the first set of imaging data including partially sampled data in a first k space; obtaining a second set of imaging data, the second set of imaging data including fully sampled data in a central region of a second k space; determining fitting data in the first k space based on the first set of imaging data and the second set of imaging data; and/or generating a target image based on the fitting data in the first k space and the first set of imaging data in the first k space.

19 Claims, 14 Drawing Sheets

600

(51) Int. Cl.

| | |
|---|---|
| *A61B 5/055* | (2006.01) |
| *G01R 33/48* | (2006.01) |
| *G01R 33/50* | (2006.01) |
| *G01R 33/54* | (2006.01) |
| *G01R 33/56* | (2006.01) |
| *G01R 33/561* | (2006.01) |
| *G01R 33/563* | (2006.01) |
| *G06T 7/00* | (2017.01) |

(52) U.S. Cl.
CPC ......... *G01R 33/4818* (2013.01); *G01R 33/54* (2013.01); *G01R 33/5616* (2013.01); *G06T 7/0012* (2013.01); *A61B 5/0035* (2013.01); *G01R 33/4828* (2013.01); *G01R 33/50* (2013.01); *G01R 33/5608* (2013.01); *G01R 33/5611* (2013.01); *G01R 33/56341* (2013.01); *G06T 2207/10081* (2013.01); *G06T 2211/424* (2013.01)

(58) Field of Classification Search
CPC .. A61B 5/0035; A61B 5/055; G01R 33/5616; G01R 33/4828; G01R 33/4818; G01R 33/50; G01R 33/5608; G01R 33/5611; G01R 33/56341; G01R 33/48; G01R 33/54

See application file for complete search history.

(56) References Cited

U.S. PATENT DOCUMENTS

| | | | |
|---|---|---|---|
| 2007/0255129 A1 | 11/2007 | Du et al. | |
| 2012/0002858 A1* | 1/2012 | Huang | ............... G01R 33/5611 |
| | | | 382/131 |
| 2012/0146640 A1 | 6/2012 | Kusahara et al. | |
| 2016/0003929 A1* | 1/2016 | Popescu | ............... G01R 33/482 |
| | | | 324/322 |
| 2018/0092569 A1* | 4/2018 | Li | ......................... G01R 33/022 |
| 2019/0011515 A1 | 1/2019 | Zheng et al. | |
| 2019/0369199 A1* | 12/2019 | Setsompop | ........ G01R 33/5616 |
| 2021/0096202 A1* | 4/2021 | Beck | .................... G01R 33/561 |

FOREIGN PATENT DOCUMENTS

| | | | | |
|---|---|---|---|---|
| CN | 108720834 A | 11/2018 | | |
| CN | 109115820 A | 1/2019 | | |
| CN | 109212443 A | 1/2019 | | |
| CN | 109767433 A | 5/2019 | | |
| CN | 110794351 A | 2/2020 | | |
| CN | 110895320 A | 3/2020 | | |
| CN | 110988765 A | 4/2020 | | |
| CN | 112712557 A | 4/2021 | | |
| CN | 112763958 A | 5/2021 | | |
| EP | 337588 B1 | * | 8/1995 | ....... G01R 33/56518 |
| EP | 3100067 B1 | * | 4/2019 | ......... G01R 33/4822 |
| EP | 3531154 A1 | | 8/2019 | |
| WO | 2017173617 A1 | | 10/2017 | |

* cited by examiner

100

110

130

Storage
Device

150

Network

120

140

141    142    143

300

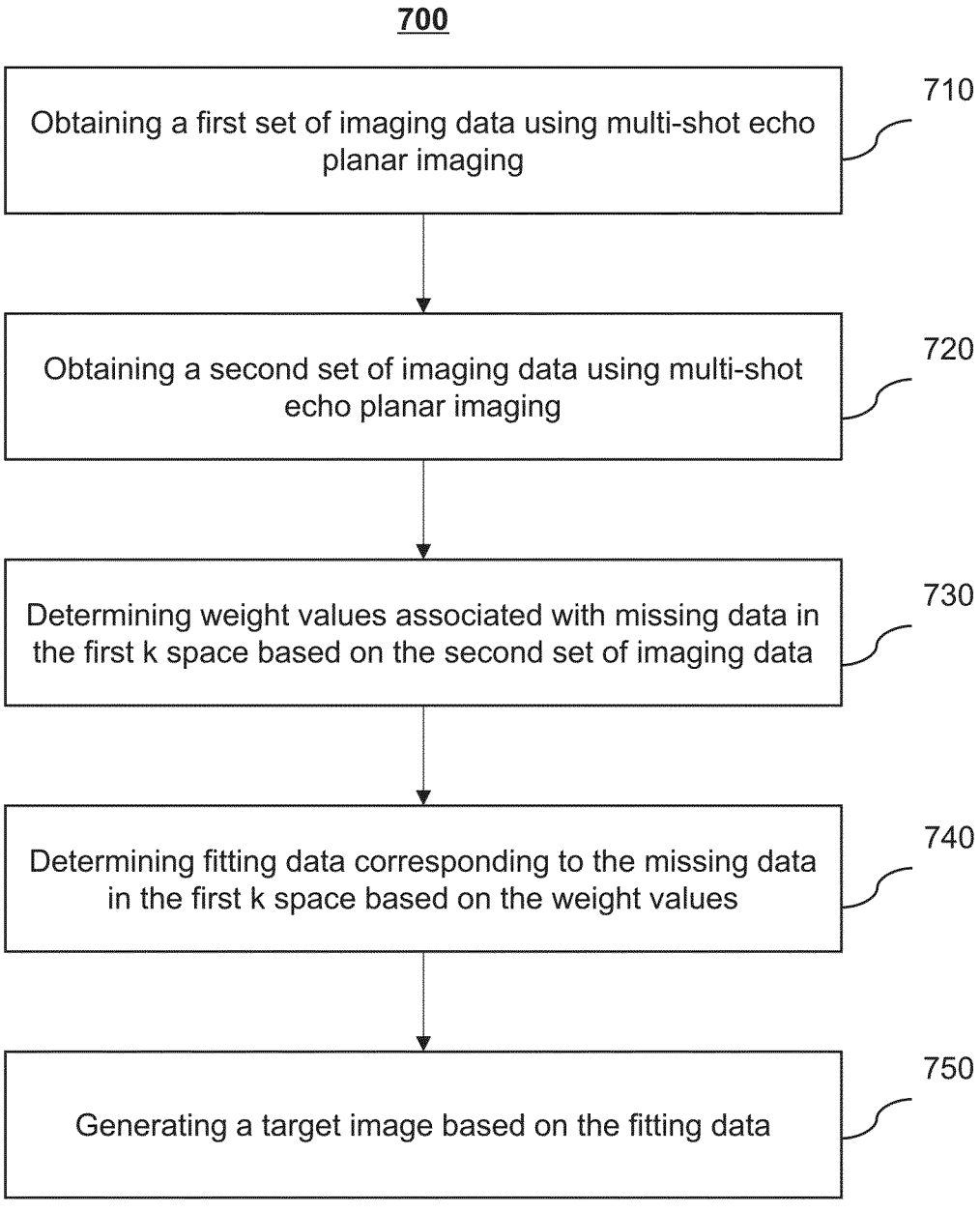

700

Obtaining a first set of imaging data using multi-shot echo planar imaging — 710

Obtaining a second set of imaging data using multi-shot echo planar imaging — 720

Determining weight values associated with missing data in the first k space based on the second set of imaging data — 730

Determining fitting data corresponding to the missing data in the first k space based on the weight values — 740

Generating a target image based on the fitting data — 750

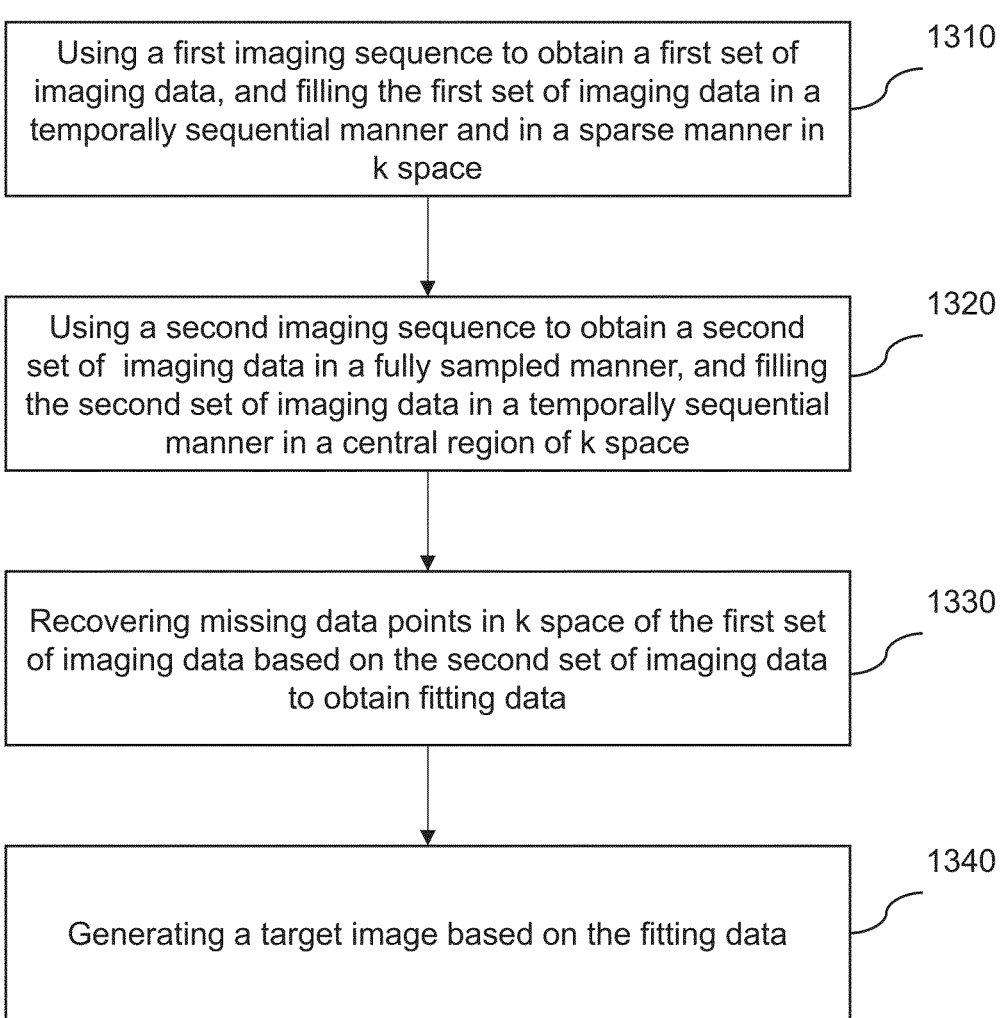

1300

Using a first imaging sequence to obtain a first set of imaging data, and filling the first set of imaging data in a temporally sequential manner and in a sparse manner in k space — 1310

Using a second imaging sequence to obtain a second set of imaging data in a fully sampled manner, and filling the second set of imaging data in a temporally sequential manner in a central region of k space — 1320

Recovering missing data points in k space of the first set of imaging data based on the second set of imaging data to obtain fitting data — 1330

Generating a target image based on the fitting data — 1340

FIG. 13

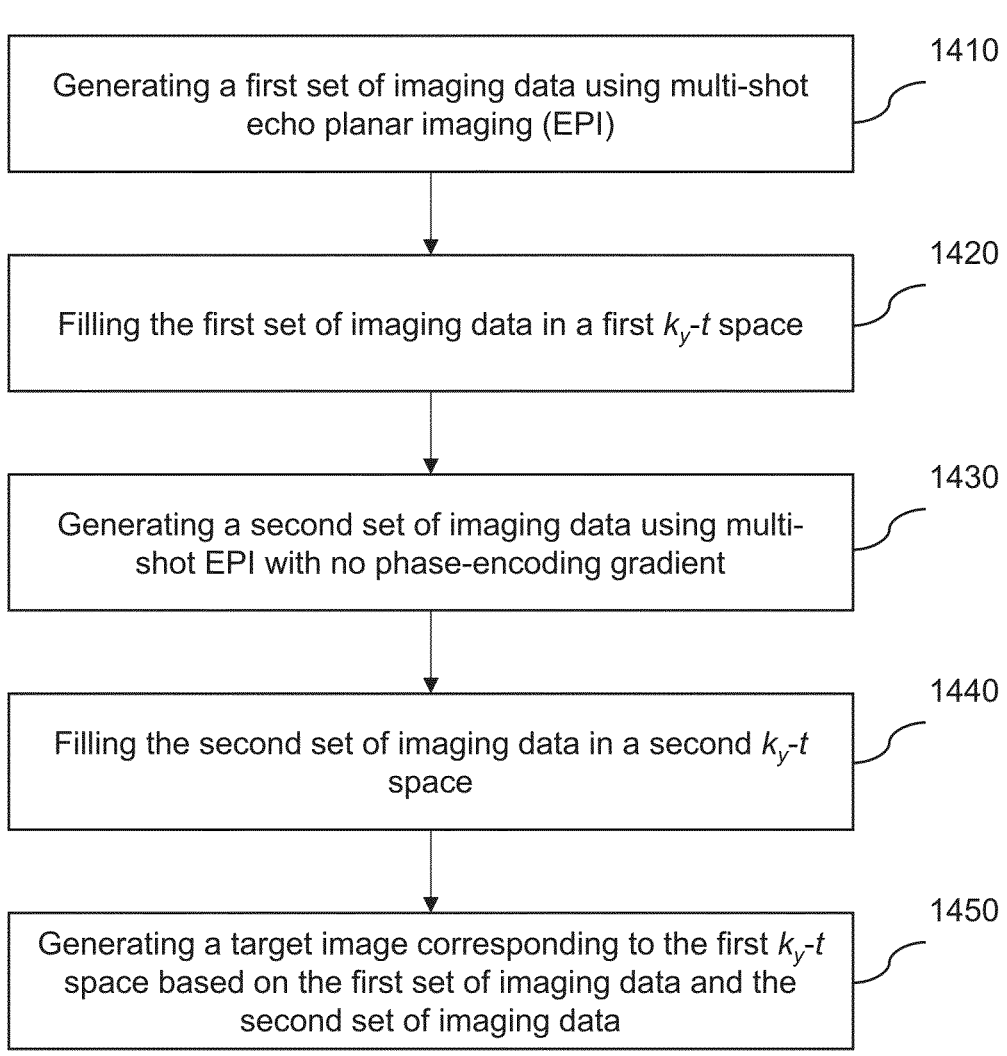

1400

Generating a first set of imaging data using multi-shot echo planar imaging (EPI) — 1410

Filling the first set of imaging data in a first $k_y$-$t$ space — 1420

Generating a second set of imaging data using multi-shot EPI with no phase-encoding gradient — 1430

Filling the second set of imaging data in a second $k_y$-$t$ space — 1440

Generating a target image corresponding to the first $k_y$-$t$ space based on the first set of imaging data and the second set of imaging data — 1450

FIG. 14

SYSTEMS AND METHODS FOR MAGNETIC RESONANCE IMAGING

CROSS-REFERENCE TO RELATED APPLICATIONS

This application claims priority of Chinese Patent Application No. 202110539454.6, filed on May 18, 2021, and the contents of which are hereby incorporated by reference.

TECHNICAL FIELD

This disclosure generally relates to systems and methods for imaging, and more particularly, relates to systems and methods for magnetic resonance imaging.

BACKGROUND

Magnetic resonance imaging (MRI) is widely used for generating images of the interior of a patient for medical diagnosis and/or treatment purposes. During an MRI process, a plurality of acquired radiofrequency (RF) signals may be filled into k space. The data in k space may be transformed to reconstruct an MRI image. MRI images generally have a good soft tissue contrast. However, the required image acquisition time for MRI is relatively long, and motion artifacts can be easily introduced into MRI images of motion sensitive organs or tissues (e.g., the heart, a lung, an abdomen, etc.). Thus, it is desired to provide systems and methods for improving imaging speed and imaging quality of magnetic resonance imaging.

SUMMARY

In one aspect of the present disclosure, a method for magnetic resonance imaging is provided. The method may include one or more operations. The one or more operations may be implemented on a computing device having one or more processors and one or more storage devices. The one or more operations may include: obtaining a first set of imaging data, the first set of imaging data being sampled in multiple shots, each shot of the multiple shots corresponding to a plurality of echo times, the first set of imaging data including partially sampled data in a first k space; obtaining a second set of imaging data, the second set of imaging data including fully sampled data in a central region of a second k space; determining fitting data in the first k space based on the first set of imaging data and the second set of imaging data; and generating a target image based on the fitting data in the first k space and the first set of imaging data in the first k space.

In some embodiments, the first k space may be a first $k_y$-t space, and/or the second k space may be a second $k_y$-t space, $k_y$ representing a phase-encoding direction, t representing an echo time direction.

In some embodiments, the first set of imaging data may be generated using multi-shot echo planar imaging.

In some embodiments, the first set of imaging data may be generated by: obtaining a first sub-set of imaging data in each shot of the multiple shots; and filling the multiple first sub-sets of imaging data in the first k space to obtain the first set of imaging data.

In some embodiments, the first sub-set of imaging data may be filled in a cyclically changing trajectory in the first k space.

In some embodiments, the first set of imaging data may be generated by sampling at different echo times and filling in different portions of the first k space.

In some embodiments, the second set of imaging data may be generated by sampling at different echo times and filling in the central region of the second k space.

In some embodiments, the second set of imaging data may be acquired with no phase-encoding gradient.

In some embodiments, the determining fitting data in the first k space based on the first set of imaging data and the second set of imaging data may include: determining weight values associated with missing data in the first k space, based on at least one portion of the second set of imaging data; and determining the fitting data corresponding to the missing data in the first k space based on the weight values and the first set of imaging data.

In some embodiments, the weight values may be characterized by determining a correspondence between the missing data in the first k space and the first set of imaging data.

In some embodiments, the determining weight values associated with missing data in the first k space may include: determining the weight values based on the at least one portion of the second set of imaging data using at least one of interpolation, a low rank method, or a machine learning model.

In some embodiments, the generating the target image may include: generating at least two echo images based on the fitting data in the first k space and the first set of imaging data in the first k space; and generating the target image based on the at least two echo images.

In another aspect of the present disclosure, a method for magnetic resonance imaging is provided. The method may include one or more operations, including: generating a first set of imaging data using multi-shot echo planar imaging (EPI), the first set of imaging data including a plurality of first sub-sets of imaging data, each first sub-set of imaging data corresponding to an EPI shot of a plurality of EPI shots; and filling the first set of imaging data in a first $k_y$-t space by filling the each first sub-set of imaging data in a cyclically changing trajectory in the first $k_y$-t space, to obtain partially sampled data in the first $k_y$-t space, $k_y$ representing a phase-encoding direction, t representing an echo time direction.

In some embodiments, each EPI shot of the plurality of EPI shots may use cyclically changing phase-encoding gradient blips, the phase-encoding gradient blips in each EPI shot may be preceded by application of a pre-winding gradient, and/or the pre-winding gradients for the plurality of EPI shots may have different gradient moments.

In some embodiments, the gradient moments of the pre-winding gradients for the plurality of EPI shots may be randomly generated.

In some embodiments, the method may further include: generating a second set of imaging data using multi-shot EPI with no phase-encoding gradient; and/or filling the second set of imaging data in a second $k_y$-t space to obtain fully sampled data in a central region of the second $k_y$-t space.

In some embodiments, the method may further include: generating a target image corresponding to the first $k_y$-t space based on the first set of imaging data and the second set of imaging data.

In some embodiments, the generating a target image may include: determining fitting data in the first $k_y$-t space based on the first set of imaging data and the second set of imaging data; and/or generating the target image based on the fitting data in the first $k_y$-t space and the first set of imaging data in the first $k_y$-t space.

In some embodiments, each data point in the first $k_y$-t space may represent an EPI readout line in a $k_x$-$k_y$ space, $k_x$ representing a readout direction.

In another aspect of the present disclosure, a system for magnetic resonance imaging is provided. The system may include at least one storage device storing a set of instructions; and at least one processor in communication with the storage device. When executing the set of instructions, the at least one processor may be configured to cause the system to perform operations including: obtaining a first set of imaging data, the first set of imaging data being sampled in multiple shots, each shot of the multiple shots corresponding to a plurality of echo times, the first set of imaging data including partially sampled data in a first k space; obtaining a second set of imaging data, the second set of imaging data including fully sampled data in a central region of a second k space; determining fitting data in the first k space based on the first set of imaging data and the second set of imaging data; and generating a target image based on the fitting data in the first k space and the first set of imaging data in the first k space.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 7 is a flowchart illustrating an exemplary process for magnetic resonance imaging according to some embodiments of the present disclosure;

FIG. 13 is a flowchart illustrating an exemplary process for generating a target image according to some embodiments of the present disclosure; and FIG. 14 is a flowchart illustrating an exemplary process for magnetic resonance imaging according to some embodiments of the present disclosure.

DETAILED DESCRIPTION

Figure 1:
FIG. 1 is a schematic diagram illustrating an exemplary MRI system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "anatomical structure" in the present disclosure may refer to gas (e.g., air), liquid (e.g., water), solid (e.g., stone), cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body. The term "an image of a subject" may be referred to as the subject for brevity.

An aspect of the present disclosure relates to a system and method for magnetic resonance imaging. According to some embodiments of the present disclosure, a processing device may obtain a first set of imaging data. The first set of imaging data may be sampled in multiple shots. Each shot of the multiple shots may correspond to a plurality of echo times. The first set of imaging data may include partially sampled data in a first k space. The processing device may obtain a second set of imaging data. The second set of imaging data may include fully sampled data in a central region of a second k space. The processing device may determine fitting data in the first k space based on the first set of imaging data and the second set of imaging data; and/or generate a target image based on the fitting data in the first k space and the first set of imaging data in the first k space.

According to the embodiments of the present disclosure, the first set of imaging data may include a plurality of first sub-sets of imaging data, and each first sub-set of imaging data may be acquired using an echo planar imaging shot. The echo planar imaging shot may use cyclically changing phase-encoding gradient blips. Accordingly, each first sub-set of imaging data may be filled in a cyclically changing trajectory in the first k space. Through using the spatio-temporal sampling trajectory (e.g., the cyclically changing trajectory), signal correlation along the phase-encoding direction and/or the echo time direction can be taken advantage of to rapidly acquire multi-contrast images. Through recovering the missing data of the first k space using the second set of imaging data, the first set of imaging data may be partially sampled, and only the central region of the second k space may need to be fully sampled, thereby saving imaging time. Thus, the imaging speed of MRI is improved, the influence of motion on imaging is reduced, and the imaging quality is improved. Besides, the multi-contrast information is provided to improve the accuracy of medical diagnosis and/or treatment processes (e.g., lesion inspection). It should be noted that different embodiments may have different effects. In different embodiments, the effects may be any one or a combination of the above, or any other effect that may be obtained.

FIG. 1 is a schematic diagram illustrating an exemplary MRI system according to some embodiments of the present disclosure. As illustrated, an imaging system 100 may include an imaging device 110, a processing device 120, a storage device 130, a terminal 140, and a network 150. The components of the imaging system 100 may be connected in one or more of various ways. Merely by way of example, as illustrated in FIG. 1, the imaging device 110 may be connected to the processing device 120 directly as indicated by the bi-directional arrow in dotted lines linking the imaging device 110 and the processing device 120, or through the network 150. As another example, the storage device 130 may be connected to the imaging device 110 directly as indicated by the bi-directional arrow in dotted lines linking the imaging device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

The imaging device 110 may be configured to acquire imaging data relating to a subject. The imaging data relating to a subject may include an image (e.g., an image slice), projection data, or a combination thereof. In some embodiments, the imaging data may be two-dimensional (2D) imaging data, three-dimensional (3D) imaging data, four-dimensional (4D) imaging data, or the like, or any combination thereof. The subject may be biological or non-biological. For example, the subject may include a patient, a man-made object, etc. As another example, the subject may include a specific portion, an organ, and/or tissue of the patient. Specifically, the subject may include the head, the neck, the thorax, the heart, the stomach, a blood vessel, soft tissue, a tumor, or the like, or any combination thereof. In the present disclosure, "object" and "subject" are used interchangeably.

In some embodiments, the imaging device 110 may include a single modality imaging device. For example, the imaging device 110 may include a magnetic resonance imaging (MRI) device (also referred to as an MR device, an MR scanner). In some embodiments, the imaging device 110 may include a multi-modality imaging device. Exemplary multi-modality imaging devices may include a PET-MRI device, or the like. The multi-modality imaging device may perform multi-modality imaging simultaneously. For example, the PET-MRI device may generate MRI data and PET data simultaneously in a single scan.

In some embodiments, the imaging device 110 may include a magnet assembly, a gradient coil assembly, and a radio frequency (RF) coil assembly. The magnet assembly may generate a first magnetic field (also referred to as a main magnetic field) for polarizing an object to be scanned. The magnet assembly may include a permanent magnet, a super-conducting conductive magnet, a resistive electromagnet, or the like.

The gradient coil assembly may generate a second magnetic field (also referred to as a gradient magnetic field). The gradient coil assembly may include an X gradient coil, a Y gradient coil, and a Z gradient coil. The gradient coil assembly may generate one or more gradient pulses on the main magnetic field in an X direction (also referred to as $G_x$), a Y direction (also referred to as $G_y$), and a Z-direction (also referred to as $G_z$) to encode the spatial information of the scanned object. In some embodiments, the X direction may also be referred to as a frequency-encoding direction or readout direction, and the Y direction may also be referred to as a phase-encoding direction. In some embodiments, $G_x$ may be used for frequency encoding or signal readout, and is commonly referred to as a frequency-encoding gradient or readout gradient. In some embodiments, $G_y$ may be used for phase encoding, and is commonly referred to as a phase-encoding gradient. In some embodiments, $G_z$ may be used for slice selection, and is commonly referred to as a slice-select gradient.

The RF coil assembly may include one or more RF transmitting coils and/or one or more RF receiving coils. The RF transmitting coil(s) may transmit an RF pulse to the object to be scanned. Under the synergy of the main magnetic field/gradient magnetic field and the RF pulse, magnetic resonance signal(s) related to the object may be generated according to a pulse sequence. The RF receiving coil may obtain the magnetic resonance signal(s) from the object according to the pulse sequence. The magnetic resonance signal(s) may also be referred to as echo signal(s). The magnetic resonance signal(s) may be filled into k space to obtain k space data. The pulse sequence may be defined by imaging parameters and arrangement of the imaging parameters in time sequence. For example, the pulse sequence may be defined by one or more parameters related to time (for example, an acquisition time (TA), an echo time (TE), a repetition time (TR), etc.). The exemplary pulse sequences may include a spin-echo sequence, a gradient echo sequence, a diffusion sequence, an inversion recovery sequence, etc., or any combination thereof. For example, the spin-echo sequence may include a fast spin-echo (FSE), a vortex spin-echo (TSE), a relaxation enhanced rapid acquisition (RARE), a half-Fourier acquisition single-shot spin-echo (HASTE), a vortex gradient spin echo (TGSE), etc., or any combination thereof. The diffusion sequence may include at least one diffusion block associated with one or more parameters of the diffusion gradient and at least one imaging block associated with one or more scanning parameters (e.g., parameters associated with one or more encoding gradients applied in the scan). In some embodiments, the pulse sequence may include a single-shot pulse sequence (e.g., a single-shot FSE, a single-shot EPI, etc.), a multi-shot pulse sequence (e.g., a multi-shot FSE, a multi-shot EPI, etc.). In some embodiments, for a single-shot pulse sequence (e.g., the single-shot FSE, the single-shot EPI, etc.), the RF pulse may be applied once in the TR, and one or more echo signals may be sampled in the TR. For the multi-shot pulse sequence (for example, the multi-shot FSE, the multi-shot EPI, etc.), the RF pulse may be applied multiple times in the TR, and one or more echo signals may be sampled in each shot.

In some embodiments, the imaging device 110 may include an analog-to-digital converter (ADC) (not shown in FIG. 1). The ADC may convert the magnetic resonance signal(s) received by one or more RF receiving coils into the magnetic resonance imaging data. The ADC may include direct conversion ADC, successive approximation ADC, ramp comparison ADC, Wilkinson ADC, integral ADC, incremental coding ADC, pipeline ADC, sigma-incremental ADC, etc., or any combination thereof.

The processing device 120 may process data and/or information obtained from the imaging device 110, the storage device 130, and/or the terminal(s) 140. For example, the processing device 120 may obtain a first set of imaging data and/or a second set of imaging data. As another example, the processing device 120 may determine fitting data based on the first set of imaging data and/or the second set of imaging data. As a further example, the processing device 120 may generate a target image based on the fitting data and/or the first set of imaging data. In some embodiments, the processing device 120 may be a single server or a server group. The server group may be centralized or distributed. In some embodiments, the processing device 120 may be local or remote. For example, the processing device 120 may access information and/or data from the imaging device 110, the storage device 130, and/or the terminal(s) 140 via the network 150. As another example, the processing device 120 may be directly connected to the imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the imaging device 110.

The storage device 130 may store data, instructions, and/or any other information. In some embodiments, the storage device 130 may store data obtained from the imaging device 110, the processing device 120, and/or the terminal(s) 140. The data may include image data acquired by the processing device 120, algorithms and/or models for processing the image data, etc. For example, the storage device 130 may store a first set of imaging data and/or a second set of imaging data. As another example, the storage device 130 may store fitting data determined by the processing device 120. As another example, the storage device 130 may store a target image determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), a high-speed RAM, etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140). One or more components in the imaging system 100 may access the data or instructions stored in the storage device 130 via the network 150. In some embodiments, the storage device 130 may be integrated into the imaging device 110.

The terminal(s) 140 may be connected to and/or communicate with the imaging device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the imaging system 100. In some embodiments, one or more components of the imaging system 100 (e.g., the imaging device 110, the processing device 120, the storage device 130, the terminal(s) 140, etc.) may communicate information and/or data with one or more other components of the imaging system 100 via the network 150. For example, the processing device 120 and/or the terminal 140 may obtain a first set of imaging data and/or a second set of imaging data from the imaging device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure.

Figure 2:
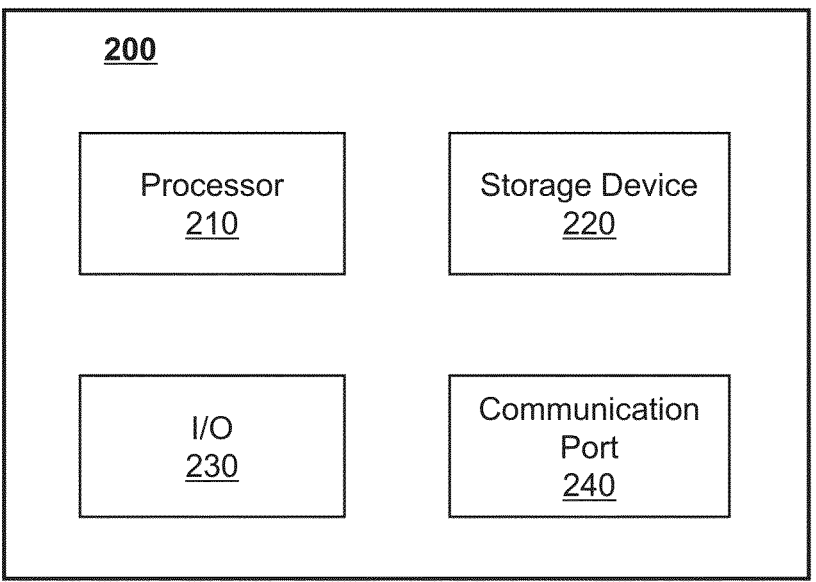
FIG. 2 is a schematic diagram illustrating exemplary hardware and/or software components of an exemplary computing device on which a processing device may be implemented according to some embodiments of the present disclosure.

FIG. 2 is a schematic diagram illustrating exemplary hardware and/or software components of an exemplary computing device on which the processing device 120 may be implemented according to some embodiments of the present disclosure. As illustrated in FIG. 2, a computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data obtained from the imaging device 110, the terminal device 140, the storage device 130, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage device 220 may store data/information obtained from the imaging device 110, the terminal device 140, the storage device 130, and/or any other component of the imaging system 100. The storage device 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the imaging device 110, the terminal device 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
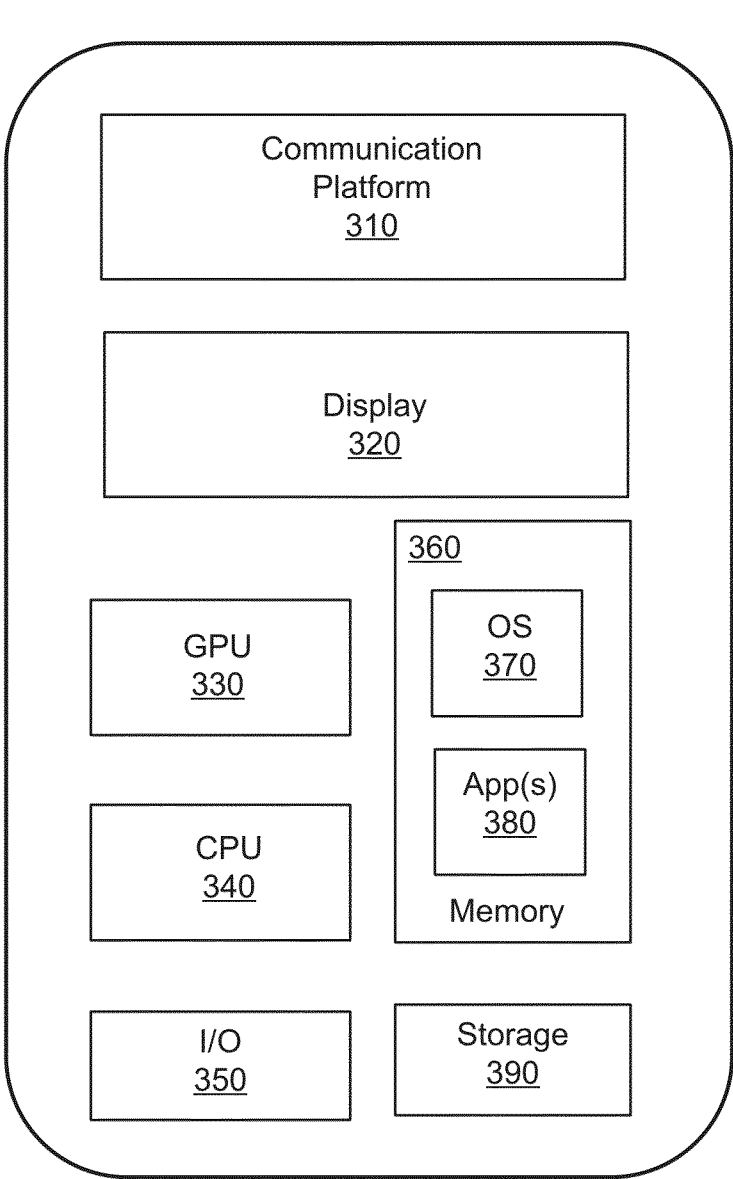
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device according to some embodiments of the present disclosure. In some embodiments, the terminal device 140 and/or the processing device 120 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the imaging system 100, and enable data and/or signal to be transmitted between the mobile device 300 and other components of the imaging system 100. For example, the communication platform 310 may establish a wireless connection between the mobile device 300 and the imaging device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the imaging system 100. For example, the communication platform 310 may transmit data and/or signals inputted by a user to other components of the imaging system 100. The inputted data and/or signals may include a user instruction. As another example, the communication platform 310 may receive data and/or signals transmitted from the processing device 120. The received data and/or signals may include imaging data acquired by the imaging device 110.

In some embodiments, a mobile operating system (OS) 370 (e.g., iOS™ Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information from the processing device 120. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
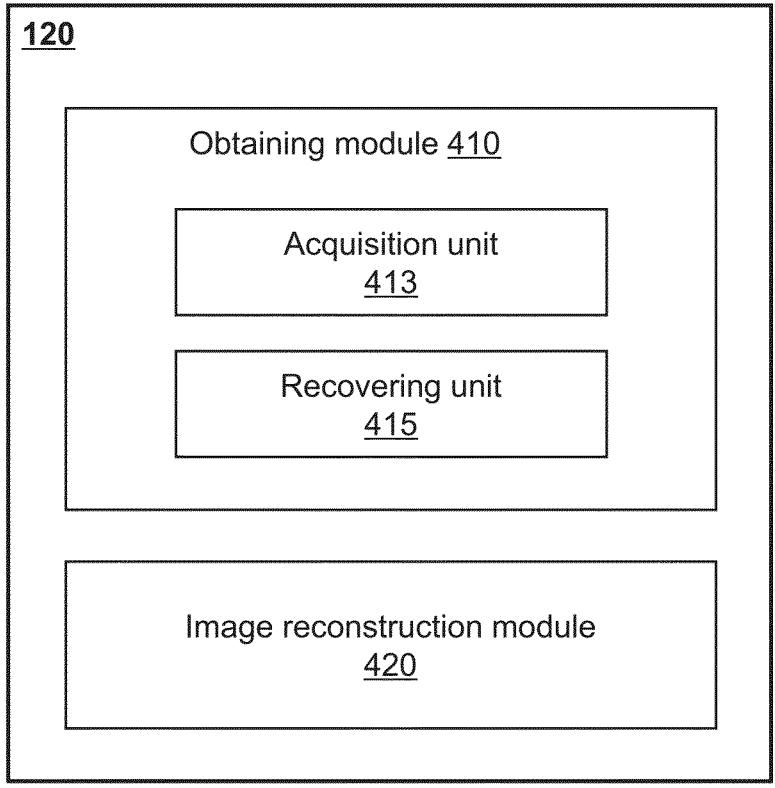
FIG. 4 is a schematic diagram illustrating an exemplary processing device according to some embodiments of the present disclosure.

FIG. 4 is a schematic diagram illustrating an exemplary processing device according to some embodiments of the present disclosure. In some embodiments, the processing device 120 may include an obtaining module 410, and an image reconstruction module 420. In some embodiments, one or more modules or units in the imaging system 100 may be connected to each other. The connection may be wireless or wired. At least a part of the imaging system 100 may be implemented on the processing device 120 or the terminal 140 as shown in FIG. 1.

In some embodiments, the obtaining module 410 may obtain imaging data (e.g., a first set of imaging data, a second set of imaging data, fitting data, etc.). In some embodiments, the obtaining module 410 may acquire imaging data from the imaging device 110. Merely by way of example, the obtaining module 410 may collect a first set of imaging data and/or a second set of imaging data using a multi-shot echo planar imaging (EPI). In some embodiments, the first set of imaging data may be generated by using one or more pulse sequences with one or more first parameters and collected by the multiple EPI shots (or the plurality of EPI shots). The first parameter(s) may include parameter(s) of one or more phase-encoding gradient sequences. The phase-encoding gradient sequence(s) may be used to implement phase-encoding gradient(s). In some embodiments, in each shot of the multiple EPI shots, a gradient direction (or gradient polarity) and/or an amplitude of the phase-encoding gradient sequence may change periodically. In some embodiments, each shot of the multiple EPI shots may use one or more phase-encoding gradient blips (also referred to as gradient pulses). The phase-encoding gradient blips may change cyclically (i.e., the gradient directions (or gradient polarities) and/or the amplitudes of the phase-encoding gradient blips may change cyclically). In some embodiments, the phase-encoding gradient blips in each EPI shot may be preceded by application of a pre-winding gradient. In some embodiments, the pre-winding gradients for different EPI shots may have different gradient moments. That is, the gradient directions, the durations, and/or amplitudes of the pre-winding gradients for different EPI shots may be different. Accordingly, the filling positions of the first set of imaging data in a first k space may be different. More descriptions of the first k space may be found elsewhere in the present disclosure (e.g., FIG. 6 and descriptions thereof).

Figure 5:
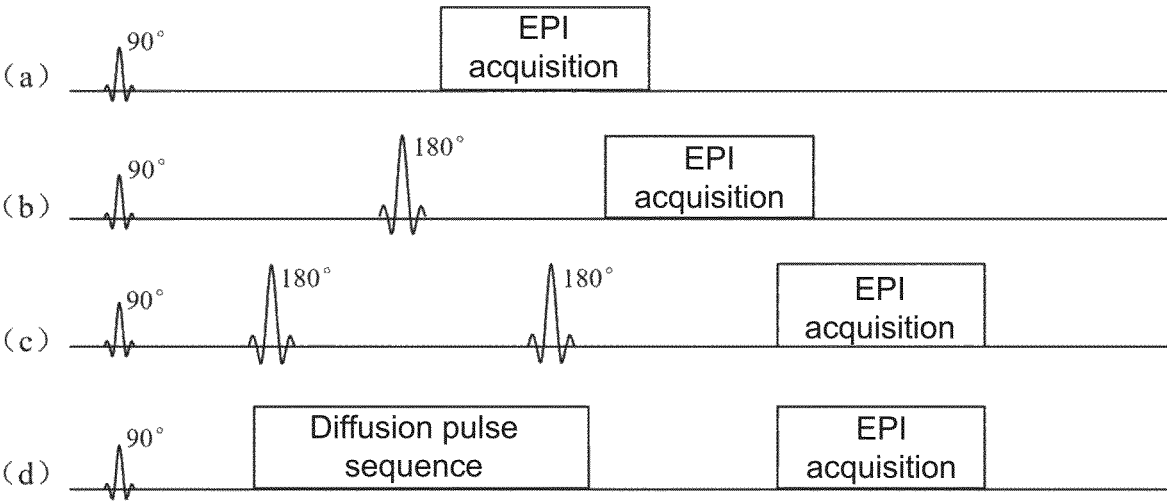
FIG. 5 is a schematic diagram illustrating exemplary EPI acquisition processes according to some embodiments of the present disclosure.

In some embodiments, the obtaining module 410 may acquire echo signal(s) (e.g., gradient echo signal(s)) after application of a 90-degree RF pulse (see, e.g., the operation (a) shown in FIG. 5). In some embodiments, the obtaining module 410 may acquire echo signal(s) (e.g., spin-echo signal(s)) after application of two successive RF pulses (e.g., a 90-degree pulse followed by a 180-degree pulse) (see, e.g., the operation (b) shown in FIG. 5). In some embodiments, the obtaining module 410 may acquire echo signal(s) (e.g., stimulated echo signal(s)) after application of three or more RF pulses (e.g., a 90-degree pulse followed by a 180-degree pulse and another 180-degree pulse) (see, e.g., the operation (c) shown in FIG. 5). In some embodiments, the obtaining module 410 may acquire echo signal(s) (e.g., diffusion echo signal(s)) after application of a 90-degree RF pulse followed by a diffusion pulse sequence (see, e.g., the operation (d) shown in FIG. 5).

In some embodiments, the obtaining module 410 may include an acquisition unit 413 and a recovering unit 415. The acquisition unit 413 may acquire imaging data (e.g., the first set of imaging data, the second set of imaging data, etc.). In some embodiments, the acquisition unit 413 may acquire imaging data using echo planar imaging (see FIG. 5). Merely by way of example, the acquisition unit 413 may obtain the first set of imaging data using multi-shot EPI based on the first parameters, and the first set of imaging data may be partially sampled in the first k space. In some embodiments, the acquisition unit 413 may fill at least a portion of the first k space with the first set of imaging data. In some embodiments, the acquisition unit 413 may obtain the second set of imaging data using multi-shot EPI based on one or more second parameters with no phase-encoding gradient, and the second set of imaging data may be fully sampled in a central region of a second k space. More descriptions of the second parameters, the second set of imaging data and the second k space may be found elsewhere in the present disclosure (e.g., FIGS. 6, 7, 13, and 14, and descriptions thereof).

The recovering unit 415 may recover data corresponding to missing data in k space. In some embodiments, the recovering unit 415 may recover fitting data based on the imaging data acquired by the acquisition unit 413. For example, the recovering unit 415 may recover fitting data based on the first set of imaging data and the second set of imaging data. In some embodiments, the recovering unit 415 may determine weight values associated with missing data in the first k space, based on the first set of imaging data and/or the second set of imaging data. The weight values may be associated with a correlation between the collected data (e.g., the first set of imaging data) and the uncollected data (e.g., the missing data) in the first k space. In some embodiments, the recovering unit 415 may use one or more algorithms to determine the weight values. Exemplary algorithms may include interpolation, a low rank method, or a machine learning model, generalized auto-calibrating partially parallel acquisition (GRAPPA) algorithm, sensitivity coding (SENSE), or simultaneous spatial harmonic imaging (SMASH) method, etc. In some embodiments, the recovering unit 415 may determine the fitting data corresponding to the missing data in the first k space based on the weight values and the first set of imaging data. More descriptions of the acquisition unit 413 and the recovering unit 415 may be found elsewhere in the present disclosure (e.g., FIGS. 6, 7, 13, and 14 and descriptions thereof).

The image reconstruction module 420 may generate one or more images (e.g., a target image). In some embodiments, the image reconstruction module 420 may generate a target image based on the fitting data and/or the first set of imaging data. In some embodiments, the target image may include, e.g., a fat quantitative map, T2 comparison map, T2 quantitative map, a susceptibility weighted imaging (SWI) comparison map, an amplitude map, a phase map, T1/R1 comparison map, T1 quantitative map, T1 fluid-attenuated inversion recovery (FLAIR) quantitative graph, a proton density (PD) comparison graph, a PD quantitative graph, $B_0$ field graph, $B_1$ field graph, a water-fat MRI/quantitative susceptibility mapping (WFI/QSM) quantitative graph, T2 comparison graph, T2/R2 quantitative graph, T2 FLAIR graph, a diffusion-weighted imaging (DWI) graph, an apparent diffusion coefficient (ADC) graph, an exponential apparent diffusion coefficient (EADC) graph, etc., or any combination. More descriptions of the image reconstruction module 420 may be found elsewhere in the present disclosure (e.g., FIGS. 6, 7, 13, and 14 and descriptions thereof).

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules or units may be added or omitted in the processing device 120. For example, the processing device 120 may further include a storage module (not shown in FIG. 4) configured to store data and/or information (e.g., imaging data, fitting data, target image) associated with the imaging system 100. As another example, the obtaining module 410 may further include a filling unit configured to fill imaging data into k space.

Figure 6:
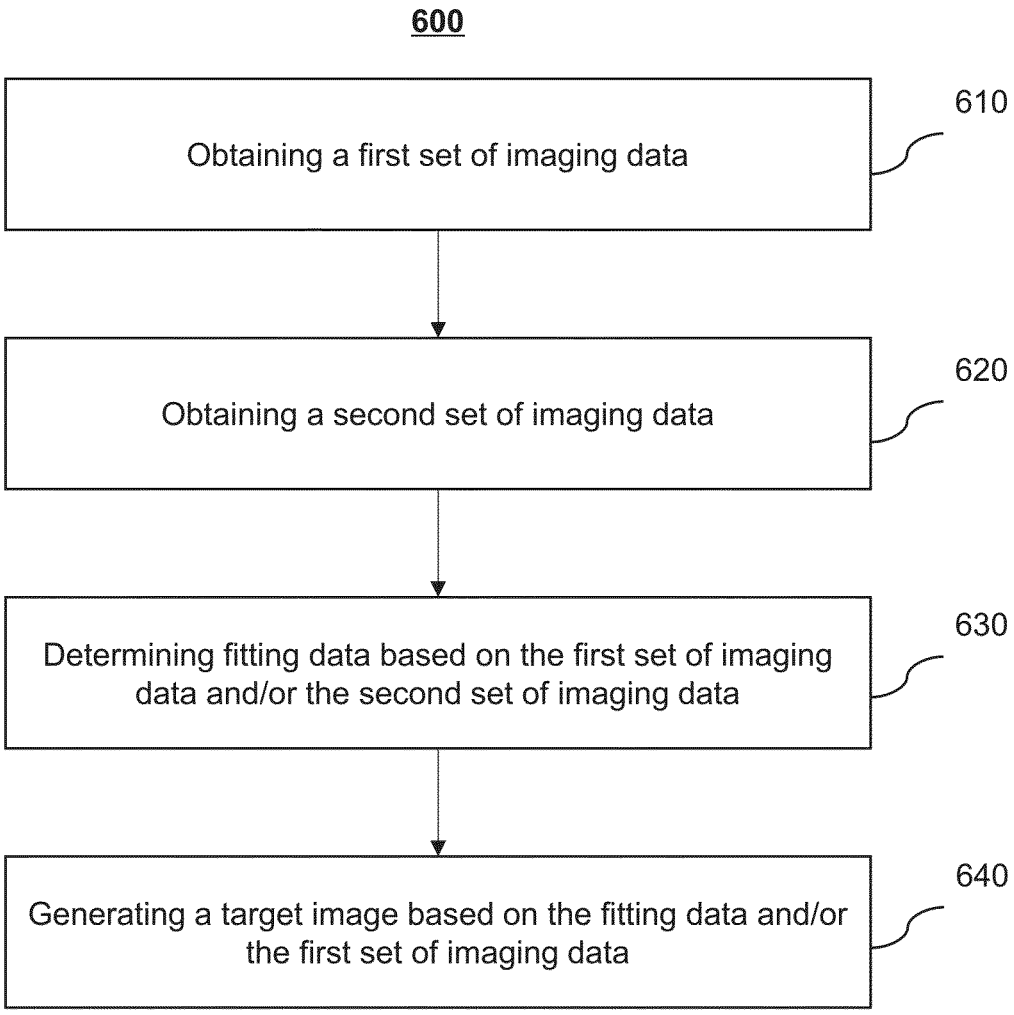
FIG. 6 is a flowchart illustrating an exemplary process for magnetic resonance imaging according to some embodiments of the present disclosure.

FIG. 6 is a flowchart illustrating an exemplary process for magnetic resonance imaging according to some embodiments of the present disclosure. In some embodiments, process 600 may be executed by the imaging system 100. For example, the process 600 may be implemented as a set of instructions (e.g., an application) stored in a storage device (e.g., the storage device 130, the storage device 220, and/or the storage 390). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 610, the processing device 120 (e.g., the obtaining module 410 (e.g., the acquisition unit 413)) may obtain a first set of imaging data.

In some embodiments, the first set of imaging data may be associated with a subject. In some embodiments, the subject may include a biological subject and/or a non-biological subject. For example, the subject may include a specific portion of a body, such as the head, the thorax, the abdomen, or the like, or any combination thereof. As another example, the subject may be a man-made composition of organic and/or inorganic matters that are with or without life.

In some embodiments, the first set of imaging data may include or may be imaging data in a first k space. In some embodiments, the first set of imaging data may include or may be partially sampled data in the first k space. In some embodiments, the first set of imaging data may be sampled in multiple shots (e.g., multiple EPI shots). In some embodiments, each shot of the multiple shots may correspond to a plurality of echo times. In some embodiments, the first set of imaging data may be filled in a portion of the first k space. In some embodiments, the first set of imaging data may be sparsely distributed in the first k space. In some embodiments, the processing device 120 may obtain a first sub-set of imaging data in each shot of the multiple shots, and fill the multiple first sub-sets of imaging data in the first k space to obtain the first set of imaging data. In some embodiments, each first sub-set of imaging data may be filled in a cyclically changing trajectory in the first k space. In some embodiments, the first set of imaging data may be generated by sampling at different echo times and filling in different portions of the first k space.

In some embodiments, the first k space may be a $k_y$-t space (also referred to as a first $k_y$-t space). $k_y$ may represent a phase-encoding direction, and t may represent an echo time direction. In some embodiments, the $k_y$-t space may be a three-dimensional (3D) k space. The axes of the 3D k space may include a phase-encoding axis (representing a phase-encoding direction), an echo time axis (representing an echo time direction), and a readout axis (representing a readout direction).

In some embodiments, the first set of imaging data may be generated or acquired using one or more imaging techniques. Exemplary imaging techniques may include spin echo imaging, fast spin echo (FSE) imaging, reduced flip angle FSE, echo planar imaging (EPI), rapid acquisition with relaxation enhancement (RARE), parallel acquisition (e.g., simultaneous acquisition of spatial harmony (SMASH), generalized autocalibrating partially parallel acquisition (GRAPPA)), etc. In some embodiments, the processing device 120 may directly obtain the first set of imaging data from the imaging device 110. In some embodiments, after generated by the imaging device 110, the first set of imaging data may be stored in a storage device (e.g., the storage device 130) of the imaging system 100, and the processing device 120 may retrieve the first set of imaging data from the storage device.

In 620, the processing device 120 (e.g., the obtaining module 410 (e.g., the acquisition unit 413)) may obtain a second set of imaging data. In some embodiments, the second set of imaging data and the first set of imaging data may be associated with a same subject.

In some embodiments, the second set of imaging data may include or may be imaging data in a second k space. In some embodiments, the second set of imaging data may include or may be fully sampled data in a central region of the second k space. In some embodiments, the second set of imaging data may be filled in the central region of the second k space. The central region may refer to a region including the center of the second k space. In some embodiments, the central region may be determined by a user (e.g., a technician) of the imaging system 100 or one or more components (e.g., the processing device 120) of the imaging system 100. In some embodiments, the second set of imaging data may be generated by sampling at different echo times and filling in the central region of the second k space. In some embodiments, the second set of imaging data may be acquired with no phase-encoding gradient.

In some embodiments, the second k space may be a $k_y$-t space (also referred to as a second $k_y$-t space). $k_y$ may represent a phase-encoding direction, and t may represent an echo time direction. In some embodiments, the $k_y$-t space may be a three dimensional k space. The axes of the three dimensional k space may include a phase-encoding axis (representing a phase-encoding direction), an echo time axis (representing an echo time direction), and a readout axis (representing a readout direction).

In some embodiments, the second set of imaging data may be generated or acquired using one or more imaging techniques. Exemplary imaging techniques may include spin echo imaging, fast spin echo (FSE) imaging, reduced flip angle FSE, echo planar imaging (EPI), rapid acquisition with relaxation enhancement (RARE), parallel acquisition (e.g., simultaneous acquisition of spatial harmony (SMASH), generalized autocalibrating partially parallel acquisition (GRAPPA)), etc. In some embodiments, the processing device 120 may directly obtain the second set of imaging data from the imaging device 110. In some embodiments, after generated by the imaging device 110, the second set of imaging data may be stored in a storage device (e.g., the storage device 130) of the imaging system 100, and the processing device 120 may retrieve the second set of imaging data from the storage device.

In 630, the processing device 120 (e.g., the obtaining module 410 (e.g., the recovering unit 415)) may determine fitting data based on the first set of imaging data and/or the second set of imaging data.

In some embodiments, the fitting data may correspond to missing data in the first k space (e.g., data that is not acquired in imaging and/or not filled into the first k space).

In some embodiments, the processing device 120 may determine fitting data in the first k space (e.g., the first $k_y$-t space) based on the first set of imaging data and/or the second set of imaging data. That is, the processing device 120 may recover the missing data based on imaging data that is already acquired.

In some embodiments, the processing device 120 may determine weight values associated with missing data in the first k space, based on the first set of imaging data and/or the second set of imaging data. In some embodiments, the processing device 120 may determine the fitting data corresponding to the missing data in the first k space based on the weight values and the first set of imaging data. In some embodiments, the weight values may relate to or be characterized by determining a correspondence between the missing data in the first k space and the first set of imaging data. In some embodiments, the weight values may be determined based on the first set of imaging data and the second set of imaging data using interpolation, a low rank method, and/or a machine learning model. More descriptions of the data recovering may be found elsewhere in the present disclosure (e.g., FIGS. 7 and 11 and descriptions thereof).

In 640, the processing device 120 (e.g., the image reconstruction module 420) may generate a target image based on the fitting data and/or the first set of imaging data.

In some embodiments, the fitting data and the first set of imaging data may form fully filled data in the first k space. In some embodiments, the fitting data and the first set of imaging data may form partially filled data in the first k space. In some embodiments, the processing device 120 may reconstruct the target image based on the fitting data and the first set of imaging data using one or more image reconstruction techniques. Exemplary image reconstruction techniques may include Fourier transform, parallel imaging reconstruction, model-based reconstruction, etc.

In some embodiments, the target image may include a quantification fat fraction map. In some embodiments, at least two echo images may be generated based on the fitting data in the first k space, the first set of imaging data in the first k space, and/or the second set of imaging data in the second k space. In some embodiments, the target image may be generated based on the at least two echo images. In some embodiments, the at least two echo images may have different contrasts.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 630 may include an operation for determining weight values and an operation for recovering data based on the weight values.

FIG. 7 is a flowchart illustrating an exemplary process for magnetic resonance imaging according to some embodiments of the present disclosure. In some embodiments, process 700 may be executed by the imaging system 100. For example, the process 700 may be implemented as a set of instructions (e.g., an application) stored in a storage device (e.g., the storage device 130, the storage device 220, and/or the storage 390). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In 710, the processing device 120 (e.g., the obtaining module 410 (e.g., the acquisition unit 413)) may obtain a first set of imaging data using multi-shot echo planar imaging (EPI).

Echo planar imaging (EPI) is an ultra-fast data acquisition technique. EPI may use fast reverse gradients to generate a series of gradient echo signals within a single relaxation time, phase-encoding the gradient echo signals respectively, and fill the gradient echo signals into a k space (e.g., a two-dimensional (2D) k space, a three-dimensional (3D) k space). EPI may include a single-shot EPI, and/or a multi-shot EPI. The single-shot EPI may use a constant phase-encoding gradient or a blipped phase-encoding gradient in imaging. In the single-shot EPI, the lines in k-space may be filled by multiple gradient reversals, producing multiple gradient echo signals in a single acquisition (also referred to as a single measurement or shot) after a single RF pulse. In the multi-shot EPI, the readout may be divided into multiple shots or segments. In some embodiments, the imaging data collected in the single-shot EPI or the multi-shot EPI may be partially sampled or fully sampled.

In some embodiments, the first set of imaging data may be obtained using multi-shot EPI based on a pulse sequence (e.g., a first pulse sequence) with one or more first parameters. In some embodiments, the first parameter(s) may include parameter(s) of one or more phase-encoding gradient sequences. In some embodiments, the phase-encoding gradient sequence(s) may be defined by one or more parameters associated with the phase-encoding gradient, including for example, an amplitude of the phase-encoding gradient, a gradient direction (or gradient polarity) of the gradient, a time point of applying the phase-encoding gradient, a duration of applying the phase-encoding gradient, etc.

In some embodiments, the amplitude and/or the gradient direction of the phase-encoding gradient may be configured to determine the distribution of the collected (or acquired) imaging data (e.g., the first set of imaging data, the second set of imaging data, etc.) in k space (e.g., the first k space). For example, the gradient direction change of two adjacent gradient blips of a phase-encoding gradient sequence may correspond to the direction change of the sampling trajectory of two adjacent data points in k space in the phase-encoding direction, and the amplitude change of the two adjacent gradient blips may correspond to the distance change of the filling positions of the two adjacent data points in the phase-encoding direction in k space. In some embodiments, the gradient direction and/or amplitude of the phase-encoding gradient in EPI acquisition may be changed periodically (or cyclically) to obtain partially sampled data in k space.

In some embodiments, in one or more EPI shots of the multi-shot EPI, one or more parameters (e.g., the gradient direction and/or the amplitude) of the gradient blips of the phase-encoding gradient sequence may change periodically (or cyclically). Alternatively or additionally, in some embodiments, in one or more EPI shots of the multi-shot EPI, one or more parameters (e.g., the gradient direction and/or the amplitude) of the gradient blips of the phase encoding gradient sequence may be the same.

Figure 8A:
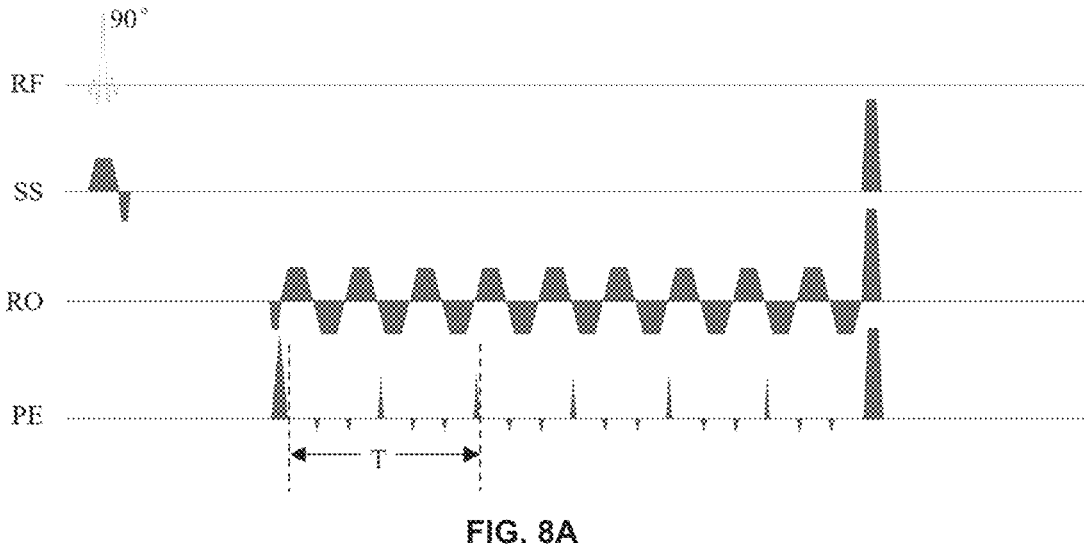
FIGS. 8A and 8B are schematic diagrams illustrating exemplary imaging sequences according to some embodiments of the present disclosure.

In some embodiments, the change period of the phase-encoding gradient in the EPI shot(s) may be adjusted according to one or more actual conditions. FIG. 8A is a schematic diagram illustrating exemplary imaging sequences according to some embodiments of the present disclosure. Exemplary imaging sequences may include RF pulse sequence(s), slice selection gradient sequence(s), readout gradient sequence(s), phase-encoding gradient sequence(s), etc. As shown in FIG. 8A, echo signal(s) (e.g., gradient echo signal(s)) may be acquired after application of an RF pulse (e.g., a 90-degree RF pulse), a slice selection (i.e., SS) gradient, a readout (i.e., RO) gradient, and a phase-encoding (i.e., PE) gradient. As shown in FIG. 8A, PE (i.e., phase-encoding) may represent the phase-encoding gradient direction, and the phase-encoding gradient sequence may include a plurality of phase-encoding gradient blips. The phase-encoding gradient blips may be preceded by application of a pre-winding gradient. Parameter(s) of the phase-encoding gradient blips may change periodically or cyclically. In FIG. 8A, T may represent a change period of the phase-encoding gradient. As shown in FIG. 8A, six phase-encoding gradient blips may be applied in a change period T of the phase-encoding gradient. In some embodiments, the six phase-encoding gradient blips may sequentially include two first gradient blips with a negative polarity, a second gradient blip with a positive polarity, two first gradient blips with a negative polarity, and a third gradient blip with a positive polarity. In some embodiments, the absolute value of the amplitude of the first gradient blip may be less than the absolute value of the amplitude of the second gradient blip, and the absolute value of the amplitude of the second gradient blip may be less than the absolute value of the amplitude of the third gradient blip. It should be noted that the pulse sequences and the gradient sequences shown in FIG. 8A is merely provided for the purposes of illustration, and not intended to limit the scope of the present disclosure. The phase-encoding gradient sequence may be any periodically changing sequence. For example, the phase-encoding gradient sequence may include any number (e.g., 3, or 5, or 7, or 10) of cycles. As another example, the gradient blips in each cycle may include 4 first gradient blips, a second gradient blip, 4 first gradient blips, and a third gradient blip. As another example, the gradient blips in each cycle may include 5 first gradient blips, 2 second gradient blips, a third gradient blip, etc. The first gradient blips, the second gradient blips, and the third gradient blips may have different amplitudes in absolute value.

In some embodiments, for each shot, an initial filling position of a filling trajectory of the first set of imaging data in k space in the phase-encoding direction may be determined based on or associated with the gradient direction and/or the amplitude of the pre-winding gradient of the phase-encoding gradient blips. In some embodiments, for different shots, the gradient directions, the durations, and/or the amplitudes (e.g., in absolute value) of the pre-winding gradients of the phase-encoding gradient blips (in different shots) may be different. In some embodiments, the gradient moments of the pre-winding gradients of the phase-encoding gradient blips (in different shots) may be different. The gradient moments of the pre-winding gradients of the phase-encoding gradient blips (in different shots) may be uniformly or nonuniformly distributed, and accordingly, the PE coordinates of the first data points (in different shots) may be uniformly or nonuniformly spaced.

In some embodiments, the first parameter(s) may further include one or more imaging parameters, the order and/or time arrangement of the pulses in the imaging sequences, etc. Exemplary imaging parameters may include parameters related to gradient fields (e.g., frequency-encoded gradient fields) generated by gradient coils, parameters related to magnetic resonance signals (e.g., echo time (TE), echo train length (ETL), spin echo type, phase variation, etc.). In some embodiments, the first parameter(s) may include an RF pulse sequence, which is characterized by parameters related to the RF pulse(s) emitted by the RF coil (e.g., the frequency of the RF pulse(s), the bandwidth of the RF pulse(s), etc.). In some embodiments, the first parameter(s) may include the number (or count) of shots or any combination of the exemplary parameters described in the present disclosure. For example, as illustrated in FIG. 8A, the first parameters may include a 90° RF pulse, slice selection (SS) gradient pulse(s), readout (RO) gradient pulse(s), and phase-encoding (PE) gradient pulse(s). Although FIG. 8A shows the imaging sequences used for one shot, the number (or count) of shots may be any other number (e.g., 2, 3, 5, 6, 7, etc.).

In some embodiments, the first set of imaging data may include partially sampled data in the first k space. In some embodiments, the first k space may be a 3D k space (e.g., a $k_x$-$k_y$-t space, $k_x$ representing a readout direction, $k_y$ representing a phase-encoding (PE) direction, t representing echo time). In some embodiments, multiple sub-sets of imaging data may be acquired using multi-shot EPI based on the first parameters, and the imaging data may be filled into the first k space to obtain the first set of imaging data. In some embodiments, the first set of imaging data may be sampled continuously in time.

Figure 10:
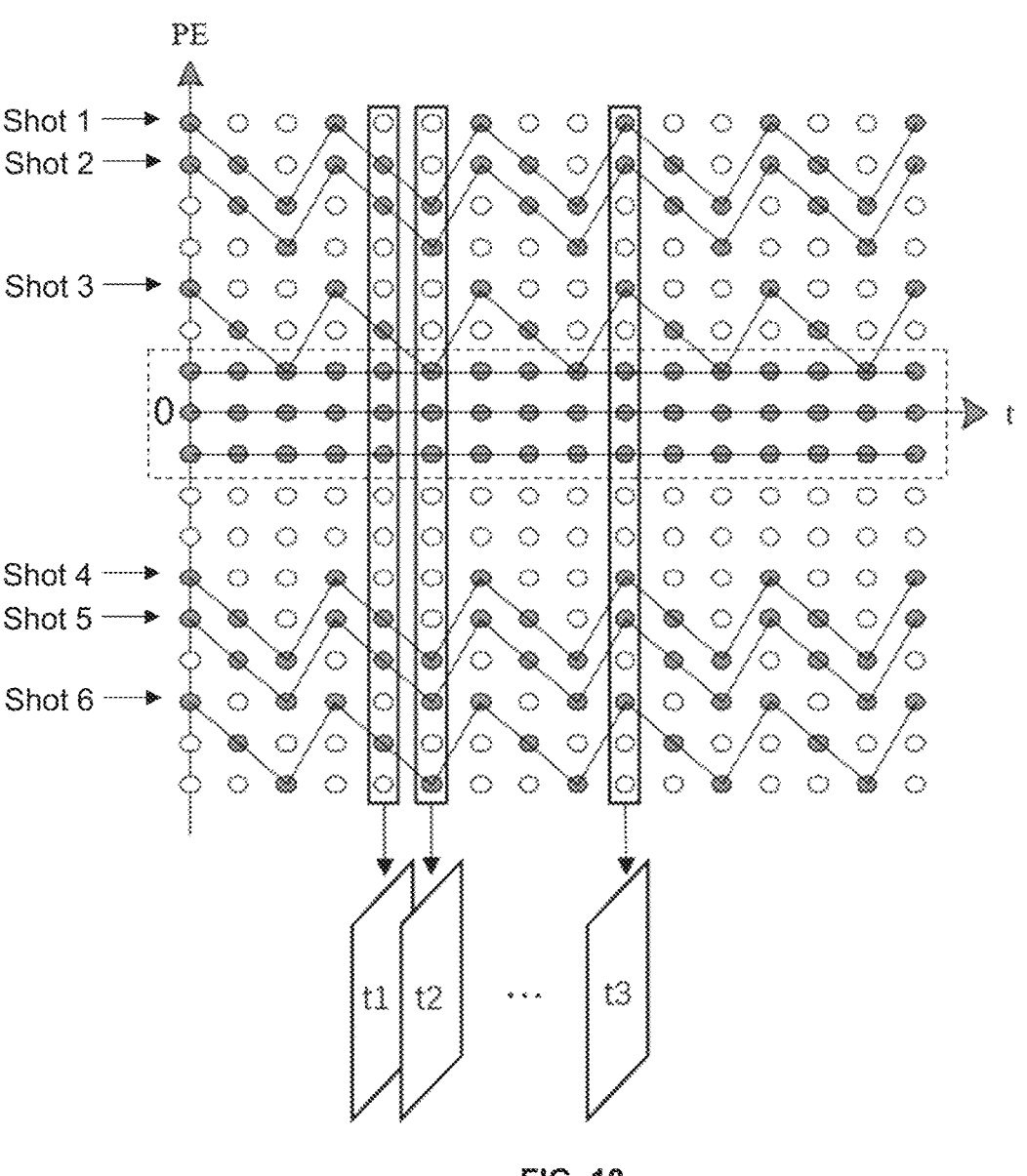
FIG. 10 is a schematic diagram illustrating exemplary imaging data filled in different k spaces according to some embodiments of the present disclosure.

In some embodiments, a sub-set of imaging data acquired in each shot may cover a part of the first k space, and the filling trajectory of the sub-set of imaging data in the first k space may change periodically. As shown in FIG. 10, six sub-sets of imaging data acquired in six shots are filled in the first k space, wherein the vertical coordinate PE represents the phase-encoding direction, the abscissa t represents the echo time TE, and the black solid points represent the collected imaging data. Each black solid point may correspond to a readout line in a $k_x$-$k_y$ space. Each black solid point may correspond to imaging data obtained using a trapezoidal pulse in the RO direction after the gradient in the PE direction is changed (e.g., as shown in FIG. 8A). As shown in FIG. 10, the blank areas indicates that no imaging data is collected. The blank areas may correspond to the missing data, and the missing data may be further recovered (see 740). For each shot, the black solid points connected by a polyline may correspond to the filling trajectory of the corresponding sub-set of imaging data. The coordinate changes in the PE direction of the collected data points in each shot may correspond to the PE gradient pulses (e.g., as shown in FIG. 8A). As shown in FIG. 10, the data points in the first k space may be continuously or sequentially distributed along the echo time direction, and the phase-encoding gradients corresponding to the data points filled at different echo times may be different.

In 720, the processing device 120 (e.g., the obtaining module 410 (e.g., the acquisition unit 413)) may obtain a second set of imaging data using multi-shot echo planar imaging (EPI).

Figure 8B:
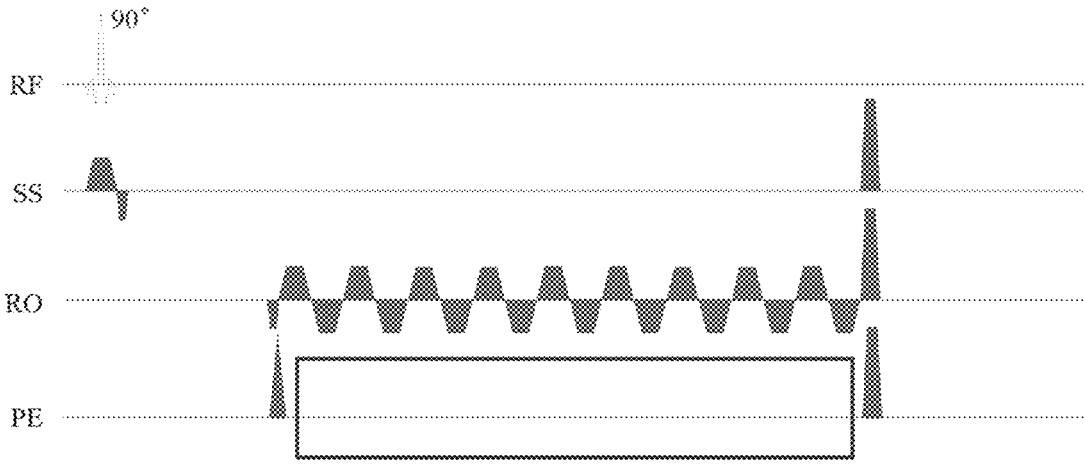
Figure 9:
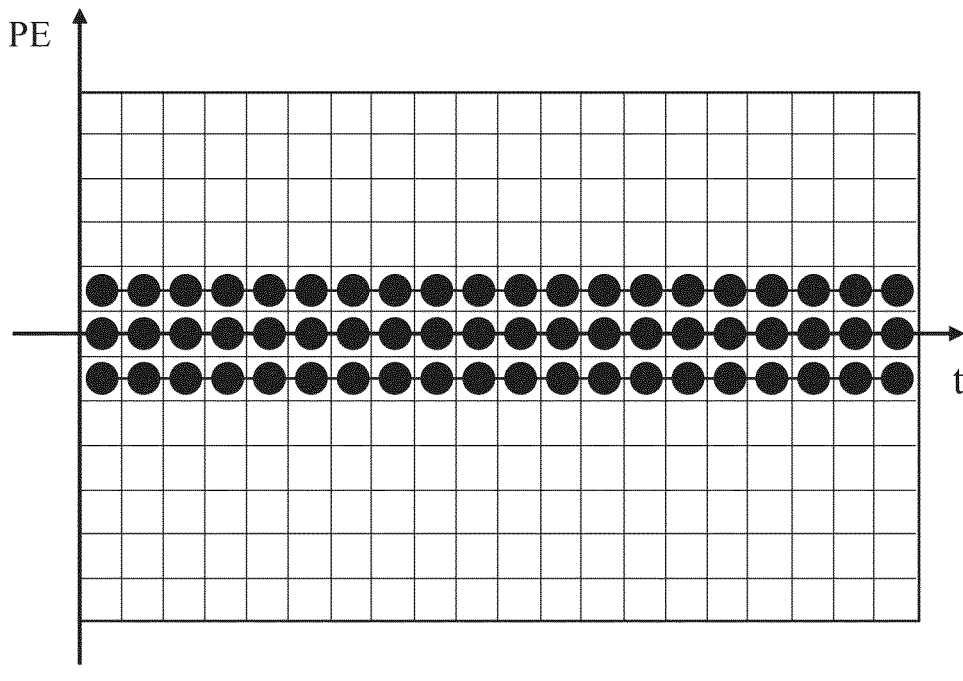
FIG. 9 is a schematic diagram illustrating exemplary imaging data filled in k space according to some embodiments of the present disclosure.

In some embodiments, second set of imaging data may be acquired using multi-shot EPI with no phase-encoding gradient. In some embodiments, the phase-encoding gradient may be turned off, i.e., the gradient magnetic field in the phase-encoding direction may be turned off. For example, as shown in FIG. 8B, no phase-encoding gradient may be applied. In some embodiments, after the phase encoding gradient is turned off, the imaging data collected in each EPI shot may be sequentially filled in k space (e.g., the second k space) along the TE direction with no shift in the PE direction. As shown in FIG. 9, the black solid points indicate the collected imaging data. Different pre-winding gradients may be used in different EPI shots, and correspondingly, the PE coordinates of the black solid points of different EPI shots may be different. The imaging data collected using multi-shot EPI (after the phase-encoding gradient is turned off) may be fully sampled data filled in a fully sampled region in the second k space. In FIG. 9, the vertical coordinate PE represents the phase-encoding direction, the abscissa t represents the echo time TE, and the black solid points represent the collected imaging data. Each black solid point may correspond to a readout line in a $k_x$-$k_y$ space.

In some embodiments, the second set of imaging data may be acquired using multi-shot EPI based on one or more second parameters. In some embodiments, the second parameter(s) may include parameters associated with one or more imaging sequences. In some embodiments, the second parameter(s) may include one or more imaging parameters, the order and/or time arrangement of the pulses in the imaging sequences, etc. In some embodiments, the second parameter(s) may include an RF pulse sequence, which is characterized by parameters related to the RF pulse(s) emitted by the RF coil (e.g., the frequency of the RF pulse(s), the bandwidth of the RF pulse(s), etc.). In some embodiments, the second parameter(s) may include the number (or count) of shots or any combination of the exemplary parameters described in the present disclosure. FIG. 8B shows a schematic diagram of exemplary imaging sequences used for one shot. The second parameters may include a 90° RF pulse, slice selection (SS) gradient pulse (s), readout (RO) gradient pulse(s), and phase-encoding (PE) gradient pulse(s). Although FIG. 8B shows the imaging sequences used for one shot, the number (or count) of shots may be any other number (e.g., 2, 3, 5, 6, 7, etc.).

In some embodiments, the number (or count) of shots for the first parameter may be different from the number (or count) of shots for the second parameter. For example, the number (or count) of shots for the second parameter may be larger than the number (or count) of shots for the first parameter. In some embodiments, the number (or count) of shots for the second parameter may be determined based on the first parameter. In some embodiments, the number (or count) of shots for the second parameter may be determined based on the coverage of the imaging data (in the first k space) collected in each shot based on the first parameter(s). For example, in FIG. 10, the imaging data (e.g., a sub-set of imaging data (acquired in shot 1 based on the first parameter (s)) in the first set of imaging data) in the first k space may longitudinally cover a number (or count) (e.g., 3) of units (or cells) of the 3D k space (e.g., the $k_x$-$k_y$-t space) along the PE direction. In some embodiments, the number (or count) of shots for the second parameter may be determined based on the number (or count) of units (or cells) (for the first parameter) covered by the imaging data (acquired in a shot) along the PE direction. The number (or count) of units (or cells) (for the first parameter) covered by the imaging data (acquired in a shot) along the PE direction may also be referred to as a covering range in the PE direction in the first k space. In some embodiments, the number (or count) of shots for the second parameter may be less than or equal to the covering range in the PE direction in the first k space. For example, if the covering range in the PE direction in the first k space is 6, the number (or count) of shots for the second parameter may be set as 2, 3, 4, 5, or 6. In some embodiments, the number (or count) of shots for the second parameter may be set as a fixed value. In some embodiments, the number (or count) of shots for the second parameter may be dynamically adjusted according to the actual needs of magnetic resonance imaging. For example, for different scanning parts and/or objects, the number (or count) of shots may be different.

In some embodiments, the gradient polarities, the durations, and/or the amplitude values of the pre-winding gradients used in acquiring the first set of imaging data may be different from those used in acquiring the second set of imaging data. In some embodiments, the gradient moments of the pre-winding gradient(s) used in acquiring the first set of imaging data may be different from those used in acquiring the second set of imaging data. In some embodiments, the gradient moments (e.g., the gradient polarities, the durations, and/or the amplitude values) of the pre-winding gradients used in multiple shots of acquiring the second set of imaging data may be different.

In some embodiments, the second set of imaging data may be or include fully sampled data in a central region of the second k space. In some embodiments, the central region may refer to the data space near the origin (or center) of the second k space. The central region filled with fully sampled data may also be referred to as the fully sampling central region. In some embodiments, the first k space and the second k space may have the same size. In some embodiments, the first set of imaging data filled in the first k space and second set of imaging data filled in the second k space may be mapped into a same k space. For example, as shown in FIG. 10, the first set of imaging data and the second set of imaging data are mapped into the mapped k space. In FIG. 10, the black solid points connected by polyline(s) correspond to the first set of imaging data acquired in multiple EPI shots (e.g., shot 1, shot 2, shot 3, shot 4, shot 5, shot 6) when the phase-encoding gradient is turned on. The black solid points connected by horizontal straight line(s) in the central region of the mapped k space correspond to the second set of imaging data acquired in multiple EPI shots when the phase-encoding gradient is turned off. The abscissa t represents the echo time TE. The imaging data acquired at a same echo time in different shots may be used to reconstruct an echo image with a contrast, and echo images corresponding to different echo times may have different contrasts. For example, as shown in FIG. 10, the imaging data acquired at echo time t1 in different shots may be used to reconstruct a first echo image with a first contrast, the imaging data acquired at echo time t2 in different shots may be used to reconstruct a second echo image with a second contrast, and the imaging data acquired at echo time t3 in different shots may be used to reconstruct a third echo image with a third contrast. The first contrast, the second contrast and the third contrast may be different.

In some embodiments, by turning off the phase-encoding gradient in collecting the second set of imaging data, the second set of imaging data in the fully sampling central region is obtained. In some embodiments, the correlation between the uncollected data (or missing data in the first k space) and the collected data (e.g., the first set of imaging data) in the first k space may be determined based on the first set of imaging data and the second set of imaging data, to recover the uncollected data (or missing data) in the first k space to obtain fitting data.

In 730, the processing device 120 (e.g., the obtaining module 410 (e.g., the recovering unit 415)) may determine weight values associated with missing data in the first k space based on the second set of imaging data (or a portion thereof).

In some embodiments, the weight values may relate to the correlation between the uncollected data (or missing data in the first k space) and the collected data (e.g., the first set of imaging data) in the first k space. In some embodiments, the weight values associated with missing data in the first k space may be determined based on at least a portion of the second set of imaging data (and/or at least a portion of the first set of imaging data) using one or more algorithms. Exemplary algorithms may include interpolation, a low rank method, a machine learning algorithm (e.g., a machine learning model), generalized auto-calibrating partially parallel acquisition (GRAPPA) algorithm, sensitivity coding (SENSE), simultaneous spatial harmonic imaging (SMASH) method, etc., or any combination thereof. In some embodiments, the machine learning model may include a neural network (e.g., convolutional neural networks (CNN), generative adversarial networks (GAN), etc., or any combination thereof).

In some embodiments, the weight values (under a training mode) of the uncollected data relative to the collected data may be determined based on at least a portion of the second set of imaging data and/or a preset rule using a preset algorithm. The preset rule may be associated with or include the training mode and one or more training areas. The training mode may be configured to determine the computation method for recovering uncollected data based on the collected data. In some embodiments, under a preset training mode, and according to one or more preset training areas (see FIG. 11), the weight values of the uncollected points relative to the collection points may be determined based on the second set of imaging data. For example, the preset training mode may include a neural network learning algorithm, and the neural network learning algorithm may be used to determine the weight values. The training area(s) may reflect the range(s) of the collected data used to determine the uncollected data. In some embodiments, the processing device 120 may determine the preset rule based on at least a portion of the first set of imaging data. For example, the training area(s) and/or training mode may be determined based on the distribution of the collected data points in the first k space.

Figure 11:
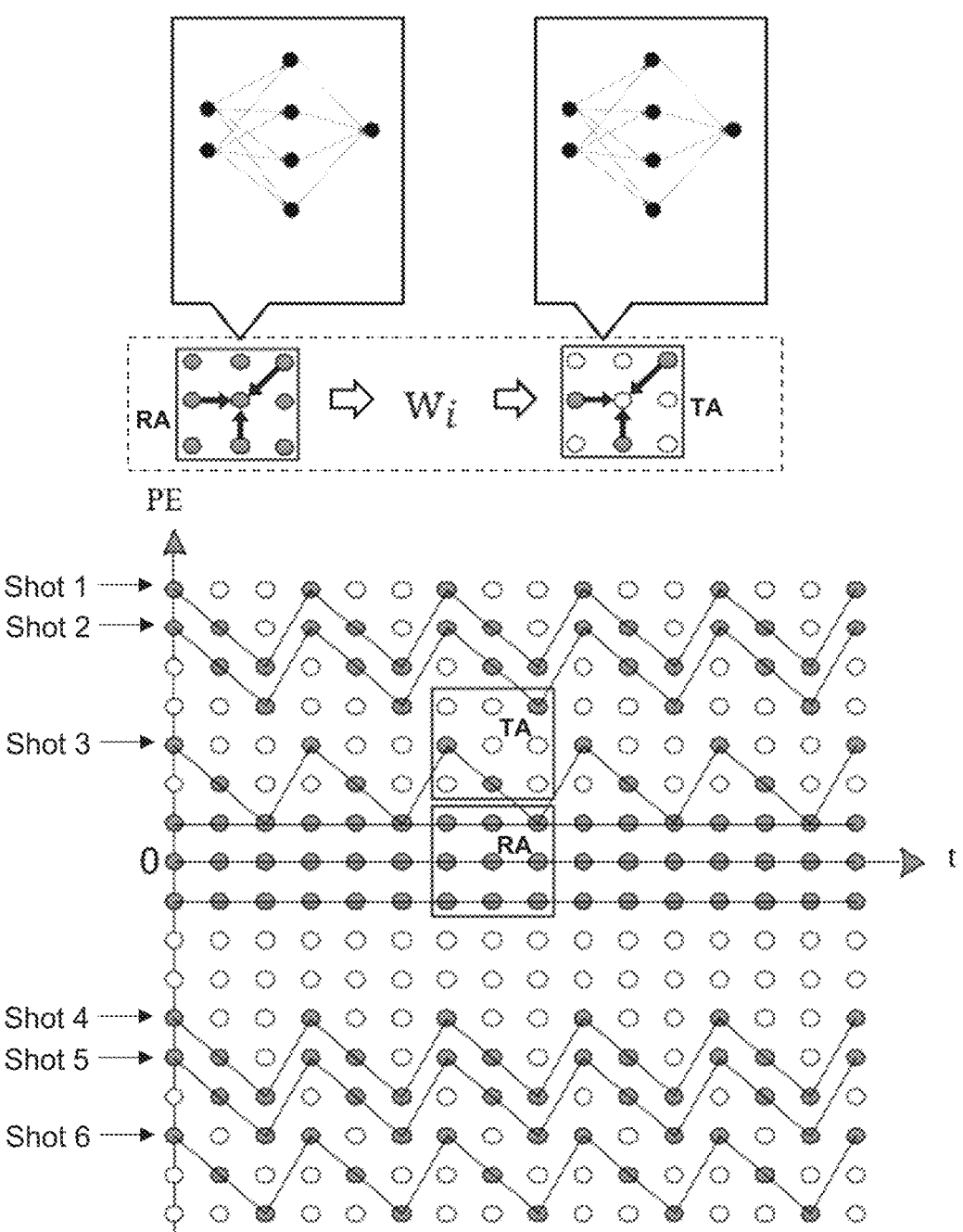
FIG. 11 is a schematic diagram illustrating an exemplary process for determining weight values associated with missing data in k space according to some embodiments of the present disclosure.

Merely by way of example, as shown in FIG. 11, the black solid points represent collected data, and the white hollow points represent uncollected data. The six sub-sets of imaging data indicated by black solid points connected by polylines illustrate the filling trajectories of the first set of imaging data acquired in six EPI shots (i.e., shot 1, shot 2, shot 3, shot 4, shot 5, shot 6). The three sub-sets of imaging data indicated by black solid points connected by horizontal straight lines illustrate the filling trajectories of the second set of imaging data that is acquired in three EPI shots when the phase-encoding gradient is turned off. A solid square frame in FIG. 11 illustrate a training area, and the training mode may be illustrated by the arrows shown in the rectangular dashed frame. As shown in FIG. 11, a reference training area marked as "RA" (e.g., with a 3×3 size) may be determined in the central region of the mapped k space in which the second set of imaging data is filled (or mapped), and a target training area marked as "TA" (e.g., with a 3×3 size) may be determined in another region of the mapped k space in which the first set of imaging data is filled (or mapped). The correlation between data in the target training area may be learned from the correlation between data in the reference training area. As shown in the rectangular dashed frame, a reference correlation (as indicated by the arrows in RA) (e.g., weight values) between a central point and three other points in the reference training area may be learned or determined, and a target correlation (as indicated by the arrows in TA) between a central point (uncollected data) and three other points (collected data) in the target training area may be designated as the reference correlation. And thus, the central point (uncollected data) can be determined based on the target correlation (e.g., weight values) and the three other points (collected data) in the target training area. It should be noted that the first set of imaging data, the second set of imaging data, the size and position of the training area(s), and the correlation indicated by the arrows shown in FIG. 11 are merely provided for the purposes of illustration, and not intended to limit the scope of the present disclosure. The reference training area and the target training area may have the same or different sizes and/or positions. For example, the reference training area and the target training area may have a same echo time range. In some embodiments, two or more reference training areas may be determined for a same target training area, and a target correlation may be determined based on two or more reference correlations from the two or more reference training areas. The two or more reference training areas may have the same or different echo time ranges and/or phase-encoding ranges. The phase-encoding range of the target training area may be the same as or different from that of the two or more reference training areas. In some embodiments, a single reference training area may be used corresponding to a plurality of target training areas. In some embodiments, the reference training area(s) may be determined randomly. In some embodiments, the reference training area and/or the target training area may have any other size, e.g., 4×4, 5×5, 3×5, 6×6, 7×7, 3×7, 5×7, 4×6, 8×8, etc.

In some embodiments, the training mode may include a neural network learning algorithm. As shown in FIG. 11, according to the training area(s) and training mode (e.g., the neural network learning algorithm, in which the neural network includes the input layer-hidden layer-output layer), the weight value $W_i$ associated with the uncollected data (i.e., the data point pointed by the arrows in TA) may be determined based on the collected data, in which i denotes a positive integer, and i≤N, N denotes the total number of echo time points.

In some embodiments, the weight values may be further optimized. For example, the weight values may be optimized based on an iterative algorithm, and an objective function $$\operatorname*{argmin}_{x} \frac{1}{2}\|P\,\mathcal{F}Sx - b\|_2^2 + \alpha R(x)$$

may be used, in which x denotes an optimization factor corresponding to the weight value $W_i$; P denotes a sampling matrix; F denotes a Fourier transform factor; S denotes a coil sensitivity of a current channel of imaging data; b denotes collected data; R denotes a sparse transformation factor; α denotes a degree of regularization; $\| \|_2^2$ denotes L2 norm; argmin denotes finding the minimum possible values given constraints.

In 740, the processing device 120 (e.g., the obtaining module 410 (e.g., the recovering unit 415)) may determine fitting data corresponding to the missing data in the first k space based on the weight values.

In some embodiments, the processing device 120 may recover the uncollected data (i.e., missing data) in the first k space and determine fitting data based on the weight values and the first set of imaging data. In some embodiments, each piece of uncollected data may correspond to one or more weight values and one or more pieces of collected data in the first set of imaging data, and a piece of fitting data corresponding to the piece of uncollected data may be determined based on the corresponding weight value(s) and corresponding piece(s) of collected data (e.g., a weighted sum of the corresponding piece(s) of collected data). In some embodiments, the weight value(s) corresponding to each piece of uncollected data may be expressed by a weight matrix, and two or more weight matrices corresponding to two or more pieces of uncollected data may be combined into a weight matrix, and accordingly, the two or more pieces of uncollected data may be recovered based on a matrix multiplication of the combined weight matrix and a matrix of corresponding collected data. For example, as shown in FIG. 11, the processing device 120 may determine the fitting data corresponding to the uncollected data (pointed by the arrows in TA) represented by the white hollow point based on the weight value $W_i$ and the collected data represented by the black solid points (in TA). In some embodiments, fully filled data in the regions of the first k space excluding the central region may be obtained based on the fitting data and the first set of imaging data, and fully filled data in the mapped k space may be obtained based on the fitting data, the first set of imaging data, and the second set of imaging data.

In 750, the processing device 120 (e.g., the image reconstruction module 420) may generate a target image based on the fitting data. In some embodiments, the processing device 120 may generate the target image based on the fitting data, the first set of imaging data, and/or the second set of imaging data. For brevity, the fitting data, the first set of imaging data, the second set of imaging data may be referred to as imaging data in the mapped k space.

In some embodiments, the processing device 120 may generate a plurality of echo images (corresponding to a plurality of echo times) based on the imaging data in the mapped k space. In some embodiments, the target image may be generated based on two or more of the plurality of echo images. In some embodiments, the processing device 120 may generate the echo images using inverse Fourier transform. In some embodiments, the echo images and/or the target image may be processed using one or more image processing algorithms. Exemplary image processing algorithms may include an expansion operation, an erosion operation, a region growing method, a level set algorithm, a gradient descent method, a single source shortest path algorithm, etc., or any combination thereof. In some embodiments, the processing device 120 may generate the target image based on the echo images using one or more reconstruction techniques. Exemplary reconstruction techniques may include a two-dimensional reconstruction technique (e.g., multi-plane reconstruction, surface reconstruction, volume reconstruction, volume rendering, etc.), a three-dimensional reconstruction technique (e.g., three-dimensional surface reconstruction, three-dimensional volume reconstruction, volume intensity projection, maximum intensity projection, minimum intensity projection, average intensity projection, etc.), or any combination thereof. In some embodiments, other reconstruction techniques that may be used may include repairing (or, rendering, filling, etc., or any combination thereof) the echo images or the target image.

Figure 12:
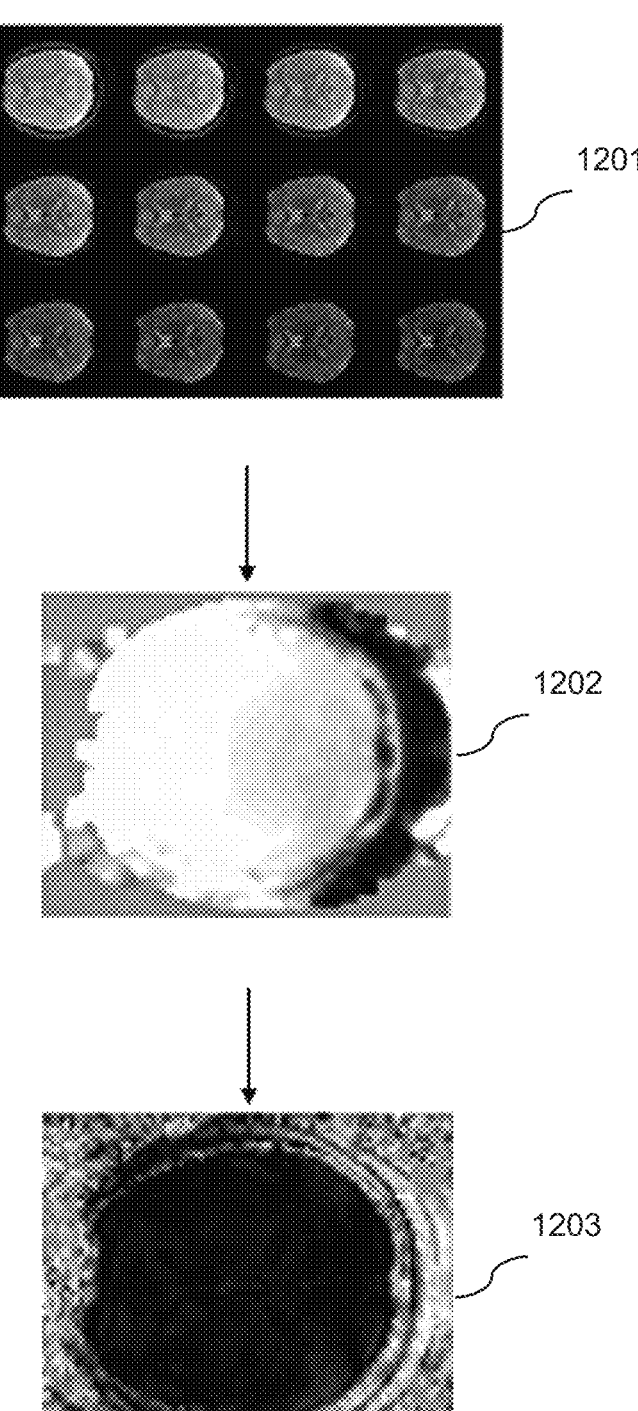
FIG. 12 is a schematic diagram illustrating an exemplary process for determining a quantification fat fraction map according to some embodiments of the present disclosure.

In some embodiments, the target image may include a quantification fat fraction map. Merely by way of example, the processing device 120 may select at least two temporally sequential echo images from the plurality of echo images to generate the fat quantitative map. For example, as shown in FIG. 12, the processing device 120 may generate 12 echo images 1201 based on the imaging data in the mapped k space, select sequential 6 echo images from the 12 echo images, extract a fat-water transition region and determine a phase distribution 1202 corresponding to the fat-water transition region, determine quantitative distribution 1203 of water and/or fat based on the fat-water transition region and the phase distribution, and generate a quantification fat fraction map based on the quantitative distribution of water and/or fat.

In some embodiments, the processing device 120 may generate an echo image based on imaging data (acquired in different shots) of the mapped k space corresponding to a same echo time. For example, as shown in FIG. 10, the processing device 120 may generate echo images corresponding to echo times t1, t2, and t3, respectively.

The processing device 120 may generate the fat quantitative map based on the at least two temporally sequential echo images (e.g., 6 echo images) using one or more algorithms. Merely by way of example, the processing device 120 may determine a global optimal solution and a local optimal solution of image signal (e.g., echo signal) for each voxel corresponding to a subject (e.g., a brain) based on 6 sequential echo images. In some embodiments, the image signal for each voxel may be expressed as:

$$S(TE_n) = (W + Fe^{-i2\pi f_F TE_n}) e^{-i2\pi \psi TE_n}, \qquad (1)$$

where $TE_n$ denotes the phase precession time or echo times of the image signal of an echo image; S denotes a pixel value corresponding to the image signal, the pixel value may be a complex value; n=1, 2, . . . , N, N denotes the number (or count) of echo times or echo images; W and F denote the amplitude of a signal associated with water and a signal associated with fat, respectively; $f_F$ denotes the difference between the proton resonance frequency of fat and water; $\psi$ denotes precession frequency, which is proportional to the strength of the main magnetic field; $2\pi f_F TE_n$ denotes the phase of the image signal corresponding to $TE_n$; $2\pi \psi TE_n$ denotes the angle of the image signal corresponding to $TE_n$.

In some embodiments, a global optimal solution may be determined. For example, according to VARPRO and/or other algorithms, $e^{-i2\pi \psi TE_n}$ may be determined based on $S(TE_n)$ in Equation (1). For example, $e^{-i2\pi \psi TE_n}$ may be determined as:

$$\Phi_G = \arg\min_{\Phi} \|(I - A(\Phi)A^+(\Phi))S\|_2^2, \qquad (2)$$

where $\Phi_G$ denotes a target phase accumulation of image signal within $\Delta TE$; $\Delta TE$ denotes an echo time difference. According to Equation (2), it may be determined that: $\rho = A^+(\Phi)S$, $\rho = [W, F]^T$, wherein $$p = e^{i2\pi \psi \Delta TE} = e^{i\Phi};$$

$$S = [S(TE_1), S(TE_2), \ldots, S(TE_n)]^T;$$

$$A(\Phi) = [A_1; A_1; \ldots; A_N]; A_n = \left[ p^{-\frac{TE_n}{\Delta TE}}, e^{-i2\pi f_F TE_n} p^{-\frac{TE_n}{\Delta TE}} \right]^T;$$

$A^+$ denotes the pseudo-inverse matrix of A; I denotes the NxN matrix.

In some embodiments, the local optimal solution may be determined based on the global optimal solution, as illustrated in Equation (3):

$$[\Phi_S, \rho_S] = \arg\min_{\Phi, \rho} \|(S - A(\Phi)\rho)\|_2^2. \qquad (3)$$

In some embodiments, the processing device 120 may determine the global optimal solution or the local optimal solution of the image signal based on a variable projection (VARPRO) algorithm, a gradient descent method, etc. Further, for all adjacent pixels in the echo image, the processing device 120 may determine whether the adjacent pixels are in a fat-water transition region and mark the fat-water transition region according to the global optimal solution and the local optimal solution. In some embodiments, for one of the solutions: $\rho=[W, F]^T$, if the absolute value of W is relatively large, the solution may also be referred to as $P_W$; if the absolute value of F is relatively large, the solution may also be referred to as $P_F$. In some embodiments, the image (e.g., an echo image) may be divided into multiple sub-regions based on the marked fat-water transition region, and the fat and water distribution in each sub-region may be determined. For example, the following Equations (4) and (5) may be configured to determine the distribution of water and fat in each sub-region:

$$C_W = \sum_{j=1}^{J} |angle(P_W(s_j) \cdot conj(P(k_j)))|, \tag{4}$$

$$C_F = \sum_{j=1}^{J} |angle(P_F(s_j) \cdot conj(P(k_j)))|, \tag{5}$$

where $C_W$ denotes the value of the objective function for the water signal; $C_F$ denotes the value of the objective function for the fat signal; j denotes the sequence number of pixels in the echo image; J denotes the total number of pixels in the echo image; $s_j$ denotes the signal value of pixel numbered as j; $k_j$ denotes the signal value of a surrounding pixel of the pixel numbered as j; angle denotes the operation of determining the phase; conj denotes conjugate operation.

In some embodiments, the processing device 120 may re-determine or verify the fat-water transition region using a region growing method based on the determination result of each sub-region, to obtain the fat quantitative map:

$$S(TE_n) = \left(W + F \sum_{q=1}^{Q} \alpha_q e^{-i2\pi f_{F,q} \cdot TE_n}\right) e^{-i2\pi\psi TE_n} \cdot e^{-\frac{TE_n}{T_2^*}}. \tag{6}$$

where q denotes the sequence number of pixels in the fat-water transition region; Q denotes the total number of pixels in the fat-water transition region; $\alpha_q$ denotes the fat-water ratio factor of the pixel numbered as q in the fat-water transition region, $\alpha_q=F/W$; $T_2^*$ denotes the time constant of the exponential decay of the echo signal.

In some embodiments, the target image may include a contrast map and/or a quantitative map of the scanned subject. For example, the target image may include a quantification fat fraction map, a T1 contrast/quantitative map, a T2 contrast/quantitative map, a proton density quantitative map, a magnetic sensitivity quantitative map, a FLAIR contrast/quantitative map, a diffusion contrast map, a static magnetic field map, and an emission field map, etc., or any combination thereof. In some embodiments, the processing device 120 may obtain different types of contrast maps and/or quantitative maps at different positions in the magnetic resonance scanner or processing device. For example, a $T_2^*$ contrast map, a $T_2^*$ quantitative map, an SWI contrast map, an amplitude map, a phase map, a T1/R1 contrast map, a T1 quantitative map, a T1 FLAIR quantitative map, a photon density (PD) contrast map, a PD quantitative map, a B0 field map, a B1 field map, a WFI\QSM quantitative map, etc., may be obtained based on the echo images of different echo times acquired according to operation (a) shown in FIG. 5. As another example, a T2 contrast map, a T2/R2 quantitative map, a T2 FLAIR map, etc., may be obtained based on the echo images of different echo times acquired according to operations (a) and/or (b) shown in FIG. 5. As a further example, a DWI map, a ADC map, an EADC map, etc., may be obtained based on echo images of different echo times acquired according to operation (d) shown in FIG. 5.

It should be noted that the above description regarding process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 710 and operation 720 may be integrated into one operation. As another example, process 700 may include one or more additional operations to determine one or more echo images.

FIG. 13 is a flowchart illustrating an exemplary process for generating a magnetic resonance image according to some embodiments of the present disclosure. In some embodiments, process 1300 may be executed by the imaging system 100. For example, the process 1300 may be implemented as a set of instructions (e.g., an application) stored in a storage device (e.g., the storage device 130, the storage device 220, and/or the storage 390). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 1300. The operations of the illustrated process presented below are intended to be illustrative. In some embodiments, the process 1300 may be accomplished with one or more additional operations not described and/or without one or more of the operations discussed. Additionally, the order of the operations of process 1300 illustrated in FIG. 13 and described below is not intended to be limiting.

In 1310, the processing device 120 (e.g., the obtaining module 410 (e.g., the acquisition unit 413)) may use a first imaging sequence to obtain a first set of imaging data, and/or fill the first set of imaging data in a temporally sequential manner and in a sparse manner in a k space (e.g., a first k space). For example, as shown in FIG. 10, the first set of imaging data may be filled at positions corresponding to black solid points in the first k space. In some embodiments, the first imaging sequence may be determined based on the first parameters. For example, as shown in FIG. 8A, the first imaging sequence may include a 90-degree RF pulse, slice selection (SS) gradient pulse(s), readout (RO) gradient pulse (s), and phase-encoding (PE) gradient pulse(s). In some embodiments, the processing device 120 may use the first imaging sequence and acquire the first set of imaging data in multiple shots.

In 1320, the processing device 120 (e.g., the obtaining module 410 (e.g., the acquisition unit 413)) may use a second imaging sequence to obtain a second set of imaging data in a fully sampled manner, and/or fill the second set of imaging data in a temporally sequential manner in a central region of a k space (e.g., a second k space). For example, as shown in FIG. 9, the second set of imaging data may be filled at positions (in the central region) corresponding to black solid points in the second k space. In some embodiments, the second imaging sequence may be determined based on the second parameters. For example, as shown in FIG. 8B, the second imaging sequence may include a 90-degree RF pulse, slice selection (SS) gradient pulse(s), readout (RO) gradient pulse(s), and phase-encoding (PE) gradient pulse (s). In some embodiments, the processing device 120 may use the second imaging sequence and acquire the second set of imaging data in multiple shots with no phase-encoding gradient.

In 1330, the processing device 120 (e.g., the obtaining module 410 (e.g., the recovering unit 415)) may recover missing data in k space of the first set of imaging data (e.g., the first k space) based on the second set of imaging data to obtain fitting data. In some embodiments, the fitting data may refer to the recovered data corresponding to the missing data in the first k space. In some embodiments, the processing device 120 may use one or more algorithms to determine weight values related to the uncollected data (i.e., the missing data) in the first k space corresponding to the first set of imaging data based on the second set of imaging data, and the uncollected data in the first k space may be recovered based on the weight values to obtain the fitting data.

In 1340, the processing device 120 (e.g., the image reconstruction module 420) may generate a target image based on the fitting data (and/or the first set of imaging data, the second set of imaging data, etc.). In some embodiments, the processing device 120 may determine one or more echo images based on the fitting data, the first set of imaging data, and/or the second set of imaging data, and generate the target image based on at least two of the echo images. More descriptions about the determination of the fitting data and the generation of the target image may be found elsewhere in the present disclosure (e.g., FIG. 7 and descriptions thereof).

It should be noted that the above description regarding process 1300 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 14 is a flowchart illustrating an exemplary process for magnetic resonance imaging according to some embodiments of the present disclosure. In some embodiments, process 1400 may be executed by the imaging system 100. For example, the process 1400 may be implemented as a set of instructions (e.g., an application) stored in a storage device (e.g., the storage device 130, the storage device 220, and/or the storage 390). In some embodiments, the processing device 120 (e.g., the processor 210 of the computing device 200, the CPU 340 of the mobile device 300, and/or one or more modules illustrated in FIG. 4) may execute the set of instructions and may accordingly be directed to perform the process 1400. The operations of the illustrated process presented below are intended to be illustrative. In some embodiments, the process 1400 may be accomplished with one or more additional operations not described and/or without one or more of the operations discussed. Additionally, the order of the operations of process 1400 illustrated in FIG. 14 and described below is not intended to be limiting.

In 1410, the processing device 120 (e.g., the obtaining module 410 (e.g., the acquisition unit 413)) may generate a first set of imaging data using multi-shot EPI. In some embodiments, the first set of imaging data may include a plurality of first sub-sets of imaging data. In some embodiments, each first sub-set of imaging data may correspond to an EPI shot of a plurality of EPI shots used in the multi-shot EPI. In some embodiments, each EPI shot of the plurality of EPI shots may include cyclically changing phase-encoding gradient blips. In some embodiments, the phase-encoding gradient blips in each EPI shot may be preceded by application of a pre-winding gradient. In some embodiments, the pre-winding gradients for the plurality of EPI shots may have different gradient moments (e.g., gradient directions, the durations, and/or amplitudes of the pre-winding gradients). In some embodiments, the gradient moments of the pre-winding gradients for the plurality of EPI shots may be randomly generated. In some embodiments, each data point in the first $k_y$-t space may represent an EPI readout line in a $k_x$-$k_y$ space. $k_x$ may represent a readout direction.

In 1420, the processing device 120 (e.g., the obtaining module 410 (e.g., the acquisition unit 413)) may fill the first set of imaging data in a first $k_y$-t space. In some embodiments, the processing device 120 may fill the first set of imaging data in the first $k_y$-t space by filling each first sub-set of imaging data in a cyclically changing trajectory in the first $k_y$-t space. In some embodiments, through filling the first set of imaging data in the first $k_y$-t space, partially sampled data in the first $k_y$-t space may be obtained. $k_y$ may represent a phase-encoding direction, and t may represent an echo time direction.

In 1430, the processing device 120 (e.g., the obtaining module 410 (e.g., the acquisition unit 413)) may generate a second set of imaging data using a plurality of EPI shots with no phase-encoding gradient.

In 1440, the processing device 120 (e.g., the obtaining module 410 (e.g., the acquisition unit 413)) may fill the second set of imaging data in a second $k_y$-t space. In some embodiments, through filling the second set of imaging data in the second $k_y$-t space, fully sampled data in a central region of the second $k_y$-t space may be obtained.

In 1450, the processing device 120 (e.g., the image reconstruction module 420) may generate a target image corresponding to the first $k_y$-t space based on the first set of imaging data and the second set of imaging data. In some embodiments, the processing device 120 may determine fitting data in the first $k_y$-t space based on the first set of imaging data and the second set of imaging data. In some embodiments, the processing device 120 may generate the target image based on the fitting data in the first $k_y$-t space, the first set of imaging data in the first $k_y$-t space, and/or the second set of imaging data in the second $k_y$-t space. More descriptions of the first or second $k_y$-t space, the $k_x$-$k_y$ space may be found elsewhere in the present disclosure (e.g., FIG. 6 and descriptions thereof). More descriptions of the determination of the fitting data and the generation of the target image may be found elsewhere in the present disclosure (e.g., FIG. 7 and descriptions thereof).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for magnetic resonance imaging, which is implemented on a computing device including at least one processor and at least one storage device, comprising:

obtaining a first set of imaging data, the first set of imaging data being sampled in multiple shots, each shot of the multiple shots corresponding to a plurality of echo times, the first set of imaging data including partially sampled data in a first k space, wherein the first set of imaging data is continuously distributed along an echo time direction, and phase-encoding gradients corresponding to data points of the first set of imaging data filled at different echo times are different;

obtaining a second set of imaging data, wherein the second set of imaging data includes fully sampled data in a central region of a second k space, and the second set of imaging data is continuously distributed along the echo time direction;

determining fitting data in the first k space based on the first set of imaging data and the second set of imaging data; and generating a plurality of echo images based on the fitting data in the first k space and the first set of imaging data in the first k space, wherein each echo image of the plurality of echo images is reconstructed by imaging data acquired at a same echo time in different shots.

2. The method of claim 1, wherein the first k space is a first $k_y$-t space, and/or the second k space is a second $k_y$-t space, $k_y$ representing a phase-encoding direction, t representing the echo time direction.

3. The method of claim 1, wherein the first set of imaging data is generated using multi-shot echo planar imaging, and the first set of imaging data is generated by:

obtaining a first sub-set of imaging data in each shot of the multiple shots; and filling the multiple first sub-sets of imaging data in the first k space to obtain the first set of imaging data.

4. The method of claim 3, wherein the first sub-set of imaging data is filled in a cyclically changing trajectory in the first k space.

5. The method of claim 1, wherein the first set of imaging data is generated by sampling at the different echo times and filling in different portions of the first k space; the second set of imaging data is generated by sampling at the different echo times and filling in the central region of the second k space, and the second set of imaging data only includes imaging data in the central region of the second k space.

6. The method of claim 1, wherein the second set of imaging data is acquired with no phase-encoding gradient.

7. The method of claim 1, wherein the determining the fitting data in the first k space based on the first set of imaging data and the second set of imaging data comprises:

determining weight values associated with missing data in the first k space, based on at least one portion of the second set of imaging data; and determining the fitting data corresponding to the missing data in the first k space based on the weight values and the first set of imaging data.

8. The method of claim 7, wherein the weight values are characterized by determining a correspondence between the missing data in the first k space and the first set of imaging data.

9. The method of claim 7, wherein the determining the weight values associated with the missing data in the first k space comprises:

determining the weight values based on a machine learning model.

10. The method of claim 1, wherein the generating the plurality of echo images comprises:

generating at least two echo images based on the fitting data in the first k space and the first set of imaging data in the first k space; and generating the plurality of echo images based on the at least two echo images.

11. The method of claim 1, wherein the second set of imaging data is acquired with slice selection gradient, readout gradient, and no phase-encoding gradient.

12. The method of claim 1, wherein a count of shots for the second set of imaging data is larger than a count of shots for the first set of imaging data.

13. The method of claim 1, wherein a count of shots for the second set of imaging data is determined based on a coverage of imaging data in the first k space that is collected in each shot of the multiple shots, or the count of shots for the second set of imaging data is dynamically adjusted, wherein for different scanning parts or objects, the count of shots for the second set of imaging data is different.

14. The method of claim 1, further comprising:

obtaining at least two temporally sequential echo images, wherein each of the echo images of the at least two temporally sequential echo images is generated by reconstructing imaging data of a mapped k space corresponding to a second same echo time through multiple excitation planar echo data acquisitions;

determining a fat-water transition region and a phase distribution of the each of the echo images of the at least two temporally sequential echo images; and determining a quantitative distribution of water and fat based on the fat-water transition region and the phase distribution of the each of the echo images of the at least two temporally sequential echo images to obtain a fat quantitative map.

15. The method of claim 14, wherein the determining the fat-water transition region and the phase distribution of the each of the echo images of the at least two temporally sequential echo images includes:

for all adjacent pixels in the each of the echo images of the at least two temporally sequential echo images, determining whether the adjacent pixels are in the fat-water transition region and marking the fat-water transition region;

dividing the each of the echo images of the at least two temporally sequential echo images into multiple subregions based on the marked fat-water transition region, and determining a fat and water distribution in each subregion to determine the fat-water transition region and the phase distribution of the each of the echo images of the at least two temporally sequential echo images.

16. A method for magnetic resonance imaging, which is implemented on a computing device including at least one processor and at least one storage device, comprising:

generating a first set of imaging data using multi-shot echo planar imaging (EPI), the first set of imaging data including a plurality of first sub-sets of imaging data, each first sub-set of imaging data corresponding to an EPI shot of a plurality of EPI shots, wherein the first set of imaging data is continuously distributed along an echo time direction, and phase-encoding gradients corresponding to data points of the first set of imaging data filled at different echo times are different;

filling the first set of imaging data in a first $k_y$-t space by filling the each first sub-set of imaging data in a cyclically changing trajectory in the first $k_y$-t space, to obtain partially sampled data in the first $k_y$-t space, $k_y$ representing a phase-encoding direction, t representing the echo time direction;

generating a second set of imaging data using multi-shot EPI with no phase-encoding gradient, the second set of imaging data is continuously distributed along the echo time direction;

filling the second set of imaging data in a second $k_y$-t space to obtain fully sampled data in a central region of the second $k_y$-t space; and generating a plurality of echo images corresponding to the first $k_y$-t space based on the first set of imaging data, wherein each echo image of the plurality of echo images is reconstructed by imaging data acquired at a same echo time in different shots.

17. The method of claim 16, wherein each EPI shot of the plurality of EPI shots uses cyclically changing phase-encoding gradient blips;

the phase-encoding gradient blips in each EPI shot are preceded by application of a pre-winding gradient;

the pre-winding gradients for the plurality of EPI shots have different gradient moments; and the gradient moments of the pre-winding gradients for the plurality of EPI shots are randomly generated.

18. The method of claim 16, wherein the generating the plurality of echo images comprising:

determining fitting data in the first $k_y$-t space based on the first set of imaging data and the second set of imaging data; and generating the plurality of echo images based on the fitting data in the first $k_y$-t space and the first set of imaging data in the first $k_y$-t space.

19. A system for magnetic resonance imaging, comprising:

at least one storage device storing a set of instructions; and at least one processor in communication with the storage device, wherein when executing the set of instructions, the at least one processor is configured to cause the system to perform operations including:

obtaining a first set of imaging data, the first set of imaging data being sampled in multiple shots, each shot of the multiple shots corresponding to a plurality of echo times, the first set of imaging data including partially sampled data in a first k space, wherein the first set of imaging data is continuously distributed along an echo time direction, and phase-encoding gradients corresponding to data points of the first set of imaging data filled at different echo times are different;

obtaining a second set of imaging data, wherein the second set of imaging data includes fully sampled data in a central region of a second k space, and the second set of imaging data is continuously distributed along the echo time direction;

determining fitting data in the first k space based on the first set of imaging data and the second set of imaging data; and generating a plurality of echo images based on the fitting data in the first k space and the first set of imaging data in the first k space, wherein each echo image of the plurality of echo images is reconstructed by imaging data acquired at a same echo time in different shots.

* * * * *